US006124125A

United States Patent [19]
Kemp et al.

[11] Patent Number: 6,124,125
[45] Date of Patent: Sep. 26, 2000

[54] AMP ACTIVATED PROTEIN KINASE

[75] Inventors: Bruce E. Kemp, Kew; David I. Stapleton, Wantirna; Kenneth I. Mitchelhill, East St. Kilda, all of Australia; Lee A. Witters, Norwich, Vt.

[73] Assignees: Trustees of Dartmouth College, Hanover, N.H.; St. Vincents Institute of Medical Research, Victoria, Australia

[21] Appl. No.: 09/101,146

[22] PCT Filed: Jan. 7, 1997

[86] PCT No.: PCT/US97/00270

§ 371 Date: Oct. 7, 1998

§ 102(e) Date: Oct. 7, 1998

[87] PCT Pub. No.: WO97/25341

PCT Pub. Date: Jul. 17, 1998

[30] Foreign Application Priority Data

Jan. 8, 1996 [AU] Australia .................................. PN7450

[51] Int. Cl.$^7$ ............................. C12N 9/12; C12N 1/20; C12N 15/00; C12N 5/00; C07H 21/04
[52] U.S. Cl. ................... 435/194; 435/252.3; 435/320.1; 435/325; 536/23.2
[58] Field of Search ............................... 435/194, 320.1, 435/252.3, 6; 536/23.2

[56] References Cited

U.S. PATENT DOCUMENTS 5,885,803  3/1999  Bandman et al. ...................... 435/69.1

FOREIGN PATENT DOCUMENTS

WO 94/28116  12/1994  WIPO .

OTHER PUBLICATIONS

Stapleton et al., J.B.C., 271, 611–614, Apr. 1996.
Aguan et al., "Characterization and chromosomal localization of the human homologue of a rat AMP–activated protein kinase–encoding gene: a major regulator of lipid metabolism in mammals", (1994) *Gene* 149, 345–350.
Carling et al., "A common bicyclic protein kinase cascade inactivates the regulatory enzymes of fatty acid and cholesterol biosynthesis", (1987) *FEBS Lett.* 223, 217–222.
Carling et al., "Mammalian AMP–activated Protein Kinasa Is Homologous to Yeast and Plant Protein Kinases Involved in the Regulation of Carbon Metabolism", (1994) *J. Biol. Chem.* 269, 11442–11448.
Celenza, J.L. and Carlson, M., "A Yeast Gene That Is Essential for Release form Glucose Repression Encodes a Protein Kinase", (1986) *Science* 233 1175–1180.
Celenza et al., "Molecular Analysis of the SNF4 Gene of *Saccharomyces cerevisiae*: Evidence for Physical Association of the SNF4 Protein Kinase", (1989) *Mol. Cell. Biol.*, 9, 5045–5054.
Corton et al., "Role of the AMP–activated protein kinase in the cellular stress response", (1994) *Current Biology* 4, 315–324.

Davies et al., "Tissue distribution of the AMP–activated protein kinase, and lack of activation by cyclic–AMP–dependent protein kinase, studied using a specific and sensitive peptide assay", (1989) *Eur. J. Biochem.* 186, 123–128.
Fields, S. and Song, O.K., "A novel genetic system to detect protein–protein interactions", (1989) *Nature*, 340, 245–246.
Ferrer et al., Activation of Rat Liver Cytosolic 3–hydroxy–3–methylglutaryl coenzymne a reductase Kinase By Adenosine 5$^1$–Monophosphate, (1985) *Biochem. Biophys. Res. Commun.* 132, 497–504.
Gao et al., "Catalytic subunits of the procine and rat 5'–AMP–activated protein kinase are members of the SNF1 protein kinase family", (1995) *Biochem. Biophys. Acta.* 1200, 73–82.
Garton et al., "Phosphorylation of bovine hormone–sensitive lipase by the AMP–activated protein kinase", (1989) *Eur. J. Biochem.* 179, 249–254.
Haygood, M.G., "Spreadsheet Macros for Coloring Sequence Alignments", (1993) *Biotechniques* 15, 1084–1089.
Kemp, B.E. and Pearson, R.B., "Design and Use of Peptide Substrates for Protein Kinases", (1991) in *Protein Phosphorylation*, Hunter, T and Sefton, B.M. (eds) Methods in Enzymology, 200, 121–134.
Kudo et al., "High Rates of Fatty Acid Oxidation during Reperfusion of Ischemic Hearts Are Associated with a Decrease in Malonyl–CoA Levels Due to an Increase in 5'–AMP–activated Protein Kinase Inhibition of Acetyl–CoA Carboxylase", (1995) *J. Biol. Chem.* 270, 17513–17520.
Lee, C.C. and Caskey, C.T., "cDNA Cloning Using Degenerate Primers", (1990) in *PCR Protocols*, (Innis, M.A. Gelfand, D.H., Srinsky, J.J., and White , T.J.
Mitchelhill et al., "Mammalian Amp–activated Protein kinase Shares Structural and Functional Homology with the Catalytic Domain of Yeast Snfl Protein Kinase", (1994) *J. Biol. Chem.* 269, 2361–2364.
Pearson, R.B., Mitchelhill, K.I., and Kemp, B.E., "Studies of protein kinase/phosphatase specificity using synthetic peptides", (1993) in *Protein Phosphorylation: A Practical Approach*, Hardie, G.D. (ed) Oxford University Press, pp. 265–291.
Schuller, H.J. and Entian, K.D., Molecular characterization of yeast regulatory gene CAT3 necessary for glucose derepression and nuclear localization of its p (1988) *Gene*, 67, 247–257.
Stapleton et al., "Mammalian 5'–AMP–activated Protein Kinase Non–catalytic Subunits Are Homologs of Proteins That Interact with Yeast Snfl Portein Kinase", (1994) *J. Biol. Chem.* 269, 29343–291346.

(List continued on next page.)

*Primary Examiner*—Rebecca E. Prouty
*Assistant Examiner*—M. Monshipouri
*Attorney, Agent, or Firm*—Law Offices of Jane Massey Licata

[57] ABSTRACT

Polynucleotides of AMPK α1, AMPK β and AMPK γ and polypeptides and biologically active fragments encoded thereby are provided. Vectors and host cells containing these polynucleotides are also provided. In addition, methods of preparing polypeptides and antibodies targeted against these polypepitdes are provided.

16 Claims, No Drawings

OTHER PUBLICATIONS

Witters, L.A. and Watts, T.D., "Yeast Acetyl–CoA Carboxylase: In Vitro Phosphorylation By Mammalian dna Yeast Protein Kinases", (1990) *Biochem. Biophys. Res. Commun.* 169, 369–376.

Woods A., et al., "Yeast SNF1 Is Functionally Related to Mammalian AMP–activated Protein Kinase and Regulates Acetyl–CoA Carboxylase in Vivo", (1994) Journal of Biol. Chem., 269, 19509–19515.

Verhoeven et al., "The AMP–activated protein kinase gene is highly expressed in rat skeletal muscle", (1995) *Eur. J. Biochem.* 228, 236–243.

Yang et al., "A Protein Kinase Substrate Identified by the Two–Hybrid System", (1992) Science, 257, 680–682.

Yang et al., "A family of proteins containing a conserved domain that mediates interaction with the yeast SNF1 protein kinase complex", (1994) *EMBO J.* 13, 5878–5886.

AMP ACTIVATED PROTEIN KINASE

This application is the National Stage of International Application No. PCT/US97/00270, filed Jan. 7, 1997, which claims the benefit of priority from Australian Patent Number 7450, filed Jan. 8, 1996.

INTRODUCTION

This invention was made in the course of research sponsored by the National Institutes of Health. The U.S. government may have certain rights in this invention.

BACKGROUND OF THE INVENTION

The present invention relates to novel AMP protein kinase subunits, to polynucleotides encoding these subunit proteins and to antibodies which bind to these subunits.

The 5'-AMP-activated protein kinase (AMPK) was initially identified as a protein kinase regulating HMG-CoA reductase (Ferrer et al. (1985) *Biochem. Biophys. Res. Commun.* 132, 497–504). Subsequently, the AMPK was shown to phosphorylate hepatic acetyl-CoA carboxylase (Carling et al. (1987) *FEBS Lett.* 223, 217–222) and adipose hormone-sensitive lipase (Garton et al. (1989) *Eur. J. Biochem.* 179, 249–254). The AMPK is therefore thought to play a key regulatory role in the synthesis of fatty acids and cholesterol.

The AMPK is believed to act as a metabolic stress-sensing protein kinase switching off biosynthetic pathways when cellular ATP levels are deleted and when 5'-AMP rises in response to fuel limitation and/or hypoxia (Corton et al. (1994) *Current Biology* 4, 315–324). Partial amino acid sequencing of hepatic AMPK (Mitchelhill et al. (1994) *J. Biol. Chem.* 269, 2361–2364; Stapleton et al. (1994) *J. Biol. Chem.* 269, 29343–29346) revealed that it consists of 3 subunits, the catalytic subunit α (63 kDa), and two non-catalytic subunits, β (40 kDa) and γ (38 kDa).

The AMPK is a member of the yeast SNF1 protein kinase subfamily that includes protein kinases present in plants, nematodes and humans. The AMPK catalytic subunit, α, has a strong sequence identity to the catalytic domain of the yeast protein kinase SNF1, which is involved in the induction of invertase (SUC2) under conditions of nutritional stress due to glucose starvation (Celenza, J. L. and Carlson, M. (1986) *Science* 233, 1175–1180). Both snf1p and the AMPK require phosphorylation by an activating protein kinase for full activity. The sequence relationship between snf1p and AMPK led to the finding that these enzymes share functional similarities, both phosphorylating and inactivating yeast acetyl-CoA carboxylase (Woods et al. (1994) *J. Biol. Chem.* 269, 19509–19516; Witters, L. A. and Watts, T. D. (1990) *Biochem. Biophys. Res. Commun.* 169, 369–376). The non-catalytic β and γ subunits of AMPK are also related to proteins that interact with snf1p; the β subunit is related to the SIP1/ SIP2 /GAL83 family of transcription regulators and the γ subunit to SNF4 (also called CAT-3) (Yang et al. (1994) *EMBO J.* 13, 5878–5886).

An isoform of the mammalian AMPK catalytic subunit has previously been cloned (Carling et al. (1994) *J. Biol. Chem.* 269, 11442–11448) and is referred to herein as AMPK $\alpha_2$. The sequence of AMPK is disclosed in WO 94/28116. The AMPK $\alpha_2$ does not complement SNF1 in yeast, indicating that their full range of functions are not identical.

A novel isoform of the mammalian AMPK catalytic subunit has now been identified and is referred to herein as AMPK $\alpha_1$. In addition, full-length cDNAs for the mammalian AMPK β and AMPK γ subunits have now been cloned and polypeptides encoded thereby purified.

SUMMARY OF THE INVENTION

Accordingly, a first aspect of the present invention provides an isolated polynucleotide which encodes mammalian AMPK $\alpha_1$ or a sequence which hybridizes thereto with the proviso that the sequence does not hybridize to mammalian AMPK $\alpha_2$ as defined in Table 1 or Table 5 of WO 94/28116. In a preferred embodiment, the polynucleotide comprises SEQ ID NO: 44. Also provided are vectors comprising such a polynucleotide, a host cell transformed with such a vector and recombinant proteins encoded by such a polynucleotide.

In a second aspect, the present invention provides a method of producing mammalian AMPK $\alpha_1$ which comprises culturing the cell including the polynucleotide of the first aspect of the present invention under conditions which allow expression of the polynucleotide encoding AMPK $\alpha_1$ and recovering the expressed AMPK $\alpha_1$.

In a third aspect, the present invention provides an oligonucleotide probe of at least 10 nucleotides, the oligonucleotide probe having a sequence such that the probe hybridizes selectively to the polynucleotide of the first aspect of the present invention. By "hybridizes selectively" it is meant that the probe does not hybridize to a polynucleotide encoding mammalian AMPK $\alpha_2$ as defined in Table 1 or Table 5 of WO 94/28116. The oligonucleotide probe may include at least about 5 contiguous nucleotides from the polynucleotide sequence which encodes amino acids 352–366. It will be understood by those of skill in the art that the oligonucleotide probes according to the third aspect of this invention may be used in a number of procedures. These include the analysis of gene regulatory elements; the analysis of gene expression in vivo; and the identification of homologous mammalian and non-mammalian cDNAs including the associated kinase-kinase.

In a fourth aspect, the present invention provides a substantially purified polypeptide encoded by a polynucleotide of the present invention or a biologically active fragment thereof with the proviso that the fragment is not present in mammalian AMPK $\alpha_2$ as defined in FIG. 3A of WO 94/28116. In a preferred embodiment, the purified polypeptide comprises at least a portion of SEQ ID NOs: 1–43. Also preferred are biologically active fragments comprising at least 8 contiguous amino acids from the sequence DFY-LATSPPDSFLDDHHLTR (SEQ ID NO: 45). By "biologically active fragment" it is meant a fragment which retains at least one of the activities of native AMPK $\alpha_1$ which activities include (i) the ability to stimulate phosphorylation of protein molecules; and (ii) the ability to mimic the binding of native AMPK $\alpha_1$ to at least one antibody or ligand molecule.

It will be appreciated by those skilled in the art that a number of modifications may be made to the polypeptides and fragments of the present invention without deleteriously effecting the biological activity of the polypeptides or fragments. This may be achieved by various changes, such as sulfation, phosphorylation, nitration and halogenation; or by amino acid insertions, deletions and substitutions, either conservative or non-conservative (e.g., D-amino acids, desamino acids) in the peptide sequence where such changes do not substantially alter the overall biological activity of the peptide. By conservative substitutions the intended combinations are: G,A; V,I,L,M; D,E; N,Q; S,T; K,R,H; F,Y,W,H; and P, Nα-alkylamino acids.

It is also possible to add various groups to the polypeptides or fragments of the present invention to confer advantages such as increased potency of extended half-life in vivo, without substantially altering the overall biological activity of the peptide.

The mammalian AMPK $\alpha_1$ polypeptide of the present invention may be used to identify compounds which regulate the action of this kinase. Such compounds are desirable since, for example, they may be used to reduce the biosynthesis of cholesterol and fatty acids. They may also be used to inhibit the release of these from intracellular stores by HSL. In addition, they may be used the reduce cellular malonyl CoA levels and promote the $\beta$-oxidation of fatty acids by the mitochondria.

Compounds may be screened for mammalian AMPK $\alpha_1$ antagonist or agonist activity by exposing mammalian AMPK $\alpha_1$ of the present invention to the compounds and assessing the activity of the mammalian AMPK $\alpha_1$. Suitable screening methods for identifying compounds which regulate the activity of mammalian AMPK $\alpha_1$ include any conventional assay systems for determining such effects. For example, a peptide containing a serine residue exclusively phosphorylated by AMP protein kinase is incubated in the presence of a preparation of AMP protein kinase and a radiolabel such as gamma $^{32}$P[ATP]. The reaction is allowed to proceed for a period of about 5 minutes and is conveniently terminated by the addition of acid. The phosphorylated peptide is conveniently separated from unincorporated radiolabel by binding to a charged membrane following washing. The degree of phosphorylation of the peptide is a measure of the activity of the mammalian AMPK $\alpha_1$.

In addition, compounds may be screened for ability to regulate expression of mammalian AMPK $\alpha_1$ in a cell by exposing the cell transformed with the polynucleotide of the first aspect of the present invention to the compound and assessing the level of expression of the polynucleotide encoding mammalian AMPK $\alpha_1$. Suitable screening methods for identifying compounds which regulate expression of mammalian AMPK $\alpha_1$ include those which involve the detection and/or determination of the amount of mammalian AMPK $\alpha_1$ or messenger RNA that encodes mammalian AMPK $\alpha_1$ or protein in the presence of the relevant test compound.

As indicated above, the compounds which regulate activity of mammalian AMPK $\alpha_1$ are considered to be of potential use in the treatment of, for example, hypercholesterolemia, hyperlipidemia, obesity, clinical syndromes associated with hypoxia or ischemia (e.g., myocardial infarction, stroke), disorders of nutrition and diabetes mellitus.

In a fifth aspect, the present invention provides an antibody which binds selectively to a polypeptide according to the fourth aspect of this invention. By "binds selectively" it is meant that the antibody does not bind to mammalian AMPK $\alpha_2$ as defined in FIG. 3A of WO 94/28116. The antibody may be a polyclonal or monoclonal antibody. It will be understood that antibodies of the present invention may be used in a number of procedures. These include monitoring protein expression in cells; the development of assays to measure kinase activity; and the precipitation of AMP protein kinase and associated proteins which may lead to characterization of these proteins.

Full-length cDNAs for the mammalian AMPK $\beta$ and AMPK $\gamma$ subunits have now been cloned. These clones have been used to characterize the tissue distribution of subunit mRNA and to express subunit protein in both bacteria and mammalian cells. Identification of their complete sequences has also led to the identification of protein families for each of these non-catalytic subunits.

Accordingly, in a sixth aspect, the present invention provides an isolated polynucleotide which encodes mammalian AMPK $\alpha$, the polynucleotide comprising a nucleic acid sequence of SEQ ID NO: 61. Also provided are vectors comprising such a polynucleotide, host cells transformed with such a vector and recombinant proteins encoded by such a polynucleotide.

In a seventh aspect, the present invention provides a method of producing mammalian AMPK $\beta$ which comprises culturing the cell including the polynucleotide of the sixth aspect of the present invention under conditions which allow expression of the polynucleotide encoding AMPK $\beta$ and recovering the expressed AMPK $\beta$.

In an eighth aspect, the present invention provides a substantially purified polypeptide, the polypeptide having an amino acid sequence of SEQ ID NO: 62.

In a ninth aspect, the present invention provides an isolated polynucleotide which encodes mammalian AMPK $\gamma$, the polynucleotide comprising a nucleic acid sequence of SEQ ID NO: 63. Also provided are vectors comprising such a polynucleotide, host cells transformed with such a vector and recombinant proteins encoded by such a polynucleotide.

In a tenth aspect, the present invention provides a method of producing mammalian AMPK $\gamma$ which comprises culturing the cell including the polynucleotide of the ninth aspect of the present invention under conditions which allow expression of the polynucleotide encoding AMPK $\gamma$ and recovering the expressed AMPK $\gamma$.

In an eleventh aspect, the present invention provides a substantially purified polypeptide, the polypeptide comprising an amino acid sequence of SEQ ID NO: 64.

DETAILED DESCRIPTION OF THE INVENTION

Mammalian AMPK, as isolated from rat and porcine liver, contains three polypeptide subunits, termed AMPK $\alpha$, AMPK $\beta$ and AMPK $\gamma$. The $\alpha$ subunit contains the kinase catalytic domain sequence and is highly homologous to several members of the SNF1 kinase family. Multiple isoforms of the $\alpha$ subunit have now been identified with $\alpha_1$ being responsible for about 90% of the AMPK activity detected in liver extracts. In addition, it has now been established that full-length AMPK $\beta$ and AMPK $\gamma$ subunits are likewise homologous to two classes of proteins in *S. cerevisiae*. This extends information previously available from limited peptide sequence analysis and from smaller PCR-derived cDNAs (Stapleton et al. (1994) *J. Biol. Chem.* 269, 29343–29346). Further, by cDNA cloning and direct peptide sequencing is has been demonstrated which isoforms of AMPK $\beta$ and AMPK $\gamma$ subunits interact with the $\alpha_1$ catalytic subunit in liver. Thus, is has now been found that these non-catalytic subunits, like the a subunit isoforms, have a wider tissue distribution, as evidenced by mRNA content of several rat tissues, than expected from the AMPK activity distribution previously reported by Gao et al. (1995) *Biochem. Biophys. Acta.* 1200, 73–82 and Davies et al. (1989) *Eur. J. Biochem.* 186, 123–128.

A novel isoform of the mammalian AMPK catalytic subunit has now been identified and is referred to herein as AMPK $\alpha_1$. The $\alpha_1$ (548 residues) and $\alpha_2$ (552 residues) isoforms of AMPK have 90% amino acid sequence identity within the catalytic core but only 61% elsewhere. The major differences in the $\alpha_1$ and $\alpha_2$ sequences occur in their COOH-terminal tails which suggests that they may interact with different proteins within this region.

It has now been found that the $\alpha_2$ 8.5 kb mRNA is most abundant in skeletal muscle with lower levels in liver, heart and kidney. In contrast, very low levels of the $\alpha_1$ 6 kb MRNA were found in all tissue except testis, where a low level of an uncharacterized 2.4 kb mRNA was observed. The low levels of $\alpha_1$ mRNA explains why the $\alpha_1$ isoform was more difficult to clone than the $\alpha_2$ isoform. The $\alpha_1$ isoform of the AMPK catalytic subunit, however, accounts for approximately 94% or more of the SAMS peptide phosphotransferase activity of rat liver and is therefore the predominant active expressed hepatic isoform.

A series of synthetic peptides including analogues of proteins not known to be substrates for the AMPK were screened with partially purified enzyme (purified to the DE-52 step). These included the myosin light chains, ADR1, glycogen synthase and phospholemman. The phospholemman peptides tested were poor substrates and not investigated further. The glycogen synthase peptide, PLSRTLS-VAAKK (SEQ ID NO: 46) was phosphorylated in an AMP-dependent manner at approximately 40% of the rate of the SAMS peptide, however, this peptide is an excellent substrate for a number of protein kinases, including protein kinase C and calmodulin dependent protein kinase II (Kemp, B. E. and Pearson, R. B. (1991) in *Protein Phosphorylation*, Hunter, T and Sefton, B. M. (eds) Methods in Enzymology, 200, 121–134). The myosin light chain peptides tested were phosphorylated with rates approximately 15% of the SAMS peptide. It was found that the ADR1 peptides ADR1 (225–234) and ADR1(222–234)$^{P229}$ were phosphorylated at rates of approximately 50% of the SAMS peptide. Results from these experiments indicate that the ADR1(222–234)$^{P229}$ peptide is phosphorylated with an apparent Km of approximately 3 $\mu$M compared to 33 $\mu$M for the SAMS peptide.

In view of the low Km of the ADR1(222–234)$^{P229}$ peptide as a substrate for the AMPK, affinity purification of the enzyme with this peptide was attempted. Initially the peptide was coupled to CNBr-activated sepharose. Although the peptide linked sepharose bound the AMPK containing fractions the enzyme could not be differentially eluted from contaminating proteins with salt gradients. In contrast when the ADR1(222–234)$^{P229}$ peptide was coupled to Pharmacia HiTrap column the AMPK was bound very tightly and required 2 M NaCl plus 30% ethylene glycol to elute it. Because the enzyme bound so tightly to this substrate affinity column it was possible to load the enzyme in buffer containing 0.5 M NaCl. The resultant purified AMPK consisted of a 63 kDa catalytic subunit and 40 kDa and 38 kDa subunits related to sip2 and snf4, respectively. In some preparations the AMPK was associated with high molecular weight material that corresponded to non-muscle myosin as assessed by tryptic peptide sequencing. An apparent purification of up to 38,000 with a yield of 15% and a recovery of 90 $\mu$g of enzyme was obtained. The fold purification may be an overestimate due to the presence of uncharacterized inhibitory material in the early fractions. The enzyme was not apparent on SDS-PAGE until the final step of purification. The avidity of the enzyme for the peptide bound to the Pharmacia HiTrap resin was greater than could be expected from the free peptide binding to the enzyme (Km 3 $\mu$M). Since the peptide linked to sepharose did not bind the enzyme as tightly it seems reasonable that the enhanced binding is due in part to the aminohexanoic acid linker between the peptide and the resin. In the case of the cAMP-dependent protein kinase there is a hydrophobic pocket between the D and G helices that is responsible for high affinity binding of the peptide inhibitor PKI. Since the ADR1(222–234)P229 peptide, LKKLTLRASFSAQ (SEQ ID NO: 47), is linked through the amine residues on its N-terminus or Lys residues, it is possible that the hydrophobic linker group has been fortuitously juxtaposed to a hydrophobic pocket on the AMPK.

In the course of sequencing the porcine AMPK it was found that the amino acid sequence of some peptides derived from the pig liver AMPK $\alpha$ subunit did not match those deduced from the rat liver cDNA sequence (Carling et al. (1994) *J. Biol. Chem.* 269, 11442–11448; Gao et al. (1995) *Biochem. Biophys. Acta.* 1200, 73–82). Therefore, the rat liver AMPK catalytic subunit, $\alpha$ was purified and peptides accounting for 40% of the protein sequenced (222/548 residues, SEQ ID NOs: 27–43). Eight of the 16 peptides contained mismatched residues with the reported AMPK cDNA sequence, but did match the pig liver enzyme sequence (SEQ ID NOs: 13–26). Using RT-PCR and cDNA library screening, a cDNA sequence of the rat hypothalamus enzyme was obtained that accounted for all of the peptide sequences of the purified rat liver AMPK catalytic subunit containing mismatches. The cDNA sequence of this AMPK catalytic subunit has been named $\alpha_1$, since it corresponds to the purified enzyme and is clearly derived from a different gene than the previously cloned $\alpha$ sequence (now referred to as $\alpha_2$). The $\alpha_1$ isoform of the AMPK catalytic subunit accounts for approximately 94% or more of the SAMS peptide phosphotransferase activity of rat liver and is therefore the predominant active expressed hepatic isoform. Despite sequencing multiple preparations of the AMPK catalytic subunit from both pig and rat liver (SEQ ID NOs 13–26 and 27–43, respectively), no peptides were obtained that matched the $\alpha_2$ isoform sequence.

Within the catalytic cores of the $\alpha_1$ and $\alpha_2$ isoforms, there is 90% amino acid identity but only 61% identity outside the catalytic core. Strong homology between the $\alpha_1$ and $\alpha_2$ sequences in the vicinity of the substrate binding groove, inferred from the protein kinase crystal structure for positions $P_{-5}$ to $P_{+5}$, suggest that the substrate specificities will be related. The substrate anchoring loop (also called the lip or activation loop) contains an insert $FL^{170}$ for $\alpha_1$, $\alpha_2$ and snf1p that may provide a hydrophobic anchor for a $P_{+3}$ or $P_{+4}$ hydrophobic residue in the peptide substrate. There is also $E^{100}$ ($E^{127}$ in cAMP-dependent protein kinase) and $D^{103}$ available for a $P_{-3}$ basic residue specificity determinant for both the $\alpha_1$, $\alpha_2$ and snf1p. Both isoforms contain a Thr-172 residue equivalent to Thr-197 in the cAMP-dependent protein kinase, which is likely to be phosphorylated and necessary for optimal activity. Since the major differences in the $\alpha_1$ and $\alpha_2$ sequences occur in their COOH-terminal tails they may interact with different proteins within this region.

Northern blot analysis of the $\beta$ and $\gamma$ subunits revealed a complex pattern of expression. The $\beta$ subunit mRNA was least abundant with similar levels across a range of tissues except brain, whereas the $\gamma$ subunit mRNA was abundant in heart, lung, skeletal muscle, liver and kidney. An earlier report on the tissue distribution of the AMPK activity had claimed that it was predominantly a liver enzyme (Davies et al. (1989) *Eur. J. Biochem.* 186, 123–128). In view of the mRNA distribution of the $\alpha_1$ and $\beta$ subunits, the tissue distribution of the AMPK activity was reassessed. The kidney contained the highest specific activity with similar levels in the liver, lung and heart and little, if any, activity in skeletal muscle. It is clear that the AMPK activity has a wider tissue distribution than appreciated heretofore, closely paralleling the distribution of $\alpha_1$ mRNA and not that of $\alpha_2$ mRNA. Using peptide specific antisera to $\alpha_1$ (residues 339–358) and $\alpha_2$ (residues 352–366) it was found that the $\alpha_2$ immunoreactivity was predominant in the heart, liver and skeletal muscle where there is also the highest concentrations of $\alpha_2$ mRNA. In contrast the $\alpha_1$ immunoreactivity is widely distributed as is the less abundant $\alpha_1$ mRNA. The antibody to $\alpha_2$ recognized a minor component in the purified $\alpha_1$ preparation but sufficient amounts of this have not been obtained to determine whether it represents weak cross reactivity with a form of $\alpha_1$, an additional isoform of the AMPK or a low level contaminant of the $\alpha_1$ preparation by the $\alpha_2$ isoform. The antibody to $\alpha_2$ does not immunoprecipitate $\alpha_1$ activity from affinity purified $\alpha_1$ AMPK. Both $\alpha_1$ and $\alpha_2$ migrate on SDS-PAGE at approximately 63 kDa. It was also found that the liver $\alpha_2$ immunoreactivity was not bound by the peptide substrate affinity column. This column specifically binds the $\alpha_1$ isoform. Using immune precipitation of the effluent from the peptide substrate affinity column with $\alpha_2$ specific antibody it was found that the $\alpha_2$ isoenzyme contained $\beta$ and $\gamma$ subunits and catalyzed the phosphorylation of the SAMS peptide. Immune precipitates of $\alpha_1$ and $\alpha_2$ showed variable activation by 5'-AMP ranging from 2–3 and 3–4 fold, respectively. There was also an approximate 60 kDa band recognized by the $\alpha_1$-specific antibody in tissue extracts from heart and lung. This band is not present in the purified liver enzyme and its relationship to the $\alpha_1$ isoform is not yet known.

The proportion of SAMS peptide phosphotransferase activity bound to the peptide affinity column with a single pass varied (ranged 90–92%, n=7 and 74–86%, n=6 rat liver preparations). With recycling, approximately 94% of the activity was bound to the column. The residual activity was attributable to $\alpha_2$ isoform activity based on immunoprecipitation with the $\alpha_2$-specific antibody. However, the amount of protein immunoprecipitated based on Coomassie blue staining indicated that there was substantially more $\alpha_2$ protein than was expected from only 6% of the total SAMS peptide activity. The apparent specific activity of the isolated rat hepatic AMPK $\alpha_2$ isoform with either the SAMS peptide or acetyl CoA carboxylase as substrate was more than 20-fold lower than the AMPK $\alpha_1$ isoform. This estimate is based on measurements using the $\alpha_2$ enriched fraction ($\alpha_1$ depleted) and quantitation by immunoblotting compared to bacterially expressed $\alpha_2$.

The specific activity of the purified $\alpha_2$ isoform is not yet known in the absence of bound antibody. Based on the $\alpha_2$ cDNA sequence, Carling et al. (1994) *J. Biol. Chem.* 269, 11442–11448 reported that a peptide specific antibody immunoprecipitated virtually all of the partially purified AMPK activity from liver. The peptide used in their experiments, PGLKPHPERMPPLI (SEQ ID NO: 48), contains 8/15 residues that are identical (underlined) between $\alpha_1$ and $\alpha_2$ so it seems reasonable that their polyclonal antisera may recognize both isoforms.

These experiments make clear that there is an isoenzyme family of AMPK $\alpha$ catalytic subunits, thus increasing the complexity of activity analysis. This also raises the question of what function the $\alpha_2$ isoform has and whether $\alpha_2$ associates with a specific subset of $\beta$ and $\gamma$ subunits. A significant fraction of the $\alpha_2$ isoform mRNA has a 142 bp out-of-frame deletion within its catalytic domain that would encode a truncated, non-functional protein (Gao et al. (1995) *Biochem. Biophys. Acta.* 1200, 73–82; Verhoeven et al. (1995) *Eur. J. Biochem.* 228, 236–243). The close sequence relationship between the $\alpha_1$ isoforms from pig, rat and human means that there is strong conservation across species. Previously, it was reported that human liver does not contain AMPK mRNA (Aguan et al. (1994) *Gene* 149, 345–350). However, it is now clear that $\alpha_2$ mRNA was being probed for and not the dominant $\alpha_1$ isoform mRNA. The gene encoding the human liver AMPK catalytic subunit reported on chromosome 1 is therefore the gene for the $\alpha_2$ isoform whereas the gene for the $\alpha_1$ isoform is located on chromosome 5. The AMPK subunit genes have now been mapped predominantly to the following chromosomal locations: $\alpha_1$, 5p12; $\beta$, 5q24.1; and $\gamma$, 12q13.1.

Recent genome sequencing has revealed multiple isoforms of the non-catalytic $\gamma$ and $\beta$ subunits of the AMPK. There appear to be at least three isoforms of the $\gamma$ subunit in brain with $\gamma_2$ and $\gamma_3$ present, distinct from the rat liver $\gamma_1$ isoform. Human brain also contains multiple $\beta$ subunit isoforms distinct from the rat liver $\beta_1$ isoform. The accession numbers for putative AMPK $\beta$ and $\gamma$ subunit isoforms are $\gamma_2$, M78939; $\gamma_3$, R52308; $\beta_2$, R20494 and $\beta_3$, R14746. Thus, a potentially large subfamily of heterotrimeric AMPKs, based on various combinations of all three AMPK subunits, may be present.

The structural relationships between the AMPK and SNF1 kinase, as well as the presence of multiple isoforms, brings into focus a vista of questions concerning the diverse physiological roles of this new subfamily of protein kinases. Whereas the AMPK regulates lipid metabolism in hepatocytes under conditions of metabolic stress, its role in other tissues, including the heart and kidney, are unknown. Recent studies have shown that the AMPK is activated during cardiac ischaemia, and the activation persists during reperfusion, possibly contributing to the ischaemia-driven decoupling of metabolism and cardiac mechanical function (Kudo et al. (1995) *J. Biol. Chem.* 270, 17513–17520).

Regulation of cardiac acetyl-CoA carboxylase by AMPK plays an important role in the switching of cardiac metabolism between the use of glucose and fatty acids as oxidative fuel. In the $\beta$ cell of the pancreas, where AMPK subunits are highly expressed in islet cells, glucose availability rapidly regulates acetyl-CoA carboxylase through changes in AMPK-directed phosphorylation, suggesting strongly a role for AMPK in stimulus-secretion coupling for insulin release. In addition to these metabolic roles, members of the SNF1 protein kinase subfamily appear to play important roles in development, with the par-1 gene of *C. elegans* playing an essential role in embryogenesis.

PCR amplification of pig and rat liver cDNA with degenerate oligonucleotides corresponding to selected AMPK $\beta$ peptide sequences yielded two major PCR products (Stapleton et al. (1994) *J. Biol. Chem.* 269, 29343–29346). One product, a rat 309 bp partial length cDNA, was used to screen a rat liver cDNA library, yielding a 1107 bp clone (SEQ ID NO: 61). The screening PCR probe corresponded to nt residues 279–588 of this sequence. This clone contains an open reading frame encoding for a 270 amino acid peptide (SEQ ID NO: 62), which contains all of the 15 independent (some overlapping) peptide sequences obtained from extensive sequence analysis of the purified protein. The translational start methionine codon is assigned from the typical Kozak sequence present for a initiation codon and the lack of any other upstream in-frame methionine codons. While no in-frame stop codon is present in this 5'-upstream sequence, a human expressed sequence tag (EST) cDNA (GenBank accession no. T78033) in the database contains such a stop codon preceding the same assigned methionine start. This reading frame, however, predicts a protein of 30,464 daltons, well below the estimated molecular weight of 40 kDa evident on SDS gel electrophoresis.

In order to clarify the size of the protein product that could be synthesized from this cDNA, the AMPK $\beta$ clone was expressed both in bacteria and mammalian cells. In both expression systems, the protein product migrates at a higher than predicted molecular weight. When purified as a His⁶-tagged fusion protein from *E. coli,* the isolated protein migrates on SDS gels with an apparent molecular weight of about 43,000 Da (the same as the ovalbumin standard). This corresponds to a AMPK β polypeptide product of 40 kDa with an additional 3 kDa daltons of fusion tag sequence derived from the pET vector. When expressed in mammalian cells from an HA-tagged expression vector, two polypeptides are evident with the major product corresponding to a 40 kDa species (after correction for the size of the HA epitope tag). A second product of 42–43 kDa is also evident using this expression system. Taken together, these data demonstrate that the protein product of this AMPK β migrates on SDS-PAGE with an anomalously high molecular weight.

Comparison of the rat liver AMPK β sequence to the database reveals that it is highly homologous to three yeast proteins (Sip1p, Sip2p and Gal83p) and to two recently cloned human EST-cDNA sequences. This alignment, as gapped according to the sequence of the *S. cerevisiase* protein, Sip1p (Yang et al. (1992) Science, 257, 680–682), is most striking at the C-terminus of AMPK β and these yeast proteins.

The AMPK β subunit is a mammalian homolog of a class of proteins in yeast, represented by Sip1p/Sip2p/Gal83p. The GAL83 gene product is known to affect glucose repression of the GAL genes. All of these proteins have been shown to interact with the Snf1p protein kinase either in the 2-hybrid system or by immunoprecipitation. It has been proposed that these proteins serve as adaptors that promote the activity of Snf1p toward specific targets. Based on analysis of yeast mutants, it has been suggested that these proteins may facilitate interaction of Snf1p with unique and different targets. Of interest is the demonstration of a highly conserved domain of about 80 amino acids in the C-terminus of Sip1p/Sip2p/Gal83p, termed the ASC domain (association with Snf1p complex) (Yang et al. (1994) *EMBO J.* 13, 5878–5886). As studied in the 2-hybrid system, the ASC domain of both Sip1p and Sip2p interacts strongly with Snf1p. However, the interaction of Sip2p with Snf1p is not entirely lost on deletion of this domain, suggesting that the ASC domain is not solely responsible for this protein-protein interaction. A putative ASC domain is also highly conserved in the C-terminus of rat liver AMPK β (aa residues 203–270), suggesting that this region may be responsible, in part, for binding to the AMPK α subunit.

AMPK β, like Sip2p and Gal83p, is phosphorylated in vitro when associated with a catalytic subunit (AMPK α or Snf1p, respectively). Mutations of Gal83p can abolish most of the Snf1p kinase activity detectable in immune complexes, precipitated with anti-Snf1p antibody. A Sip2p/E gal 83/E mutant shows reduced Snf1 protein kinase activity, that is restored following expression of either Sip2p or Gal83p LexA-fusion proteins in the mutant strain (Yang et al. (1994) *EMBO J.* 13, 5878–5886). Taken together, these data suggest the possibility that AMPK β may also serve as an adaptor molecule for the AMPK α catalytic unit and will positively regulate AMPK activity.

AMPK β appears to have anomalous migration on SDS gels, with the polypeptide migrating at a $M_r$ approximately 10 kDa larger than the size predicted from the cDNA. This slower migration is evident for both the bacterially expressed His⁶-fusion protein and for the protein expressed in COS7 cells. These observations suggest that higher orders of structure are responsible for the anomalous migration on SDS-PAGE. The AMPK β subunit is autophosphorylated in vitro; this suggests that the two AMPK β bands expressed on transfection of mammalian cells with AMPK β cDNA may result from a similar post-translational modification giving rise to smaller mobility shifts. Interestingly, this aberrant migratory behavior of AMPK β is similar to that of its yeast homolog, Gal83p. The LexA-fusion protein(s) of Gal83, as expressed in yeast, also migrate at greater than the expected molecular weight and display more than one band on SDS gels, consistent with the known phosphorylation of Gal83p by Snf1p. Mass spectrometry analysis of the β-subunit indicates that the amino terminal glycine is myristylated and that the subunit is isolated in mono- and di- phosphorylated forms.

Using the MOPAC procedure and other PCR amplification protocols, a 192 bp cDNA corresponding to rat liver AMPK γ sequence was obtained and used for library screening to obtain a partial length rat liver cDNA of approximately 1.3 kb. This sequence did not contain either a start methionine codon or all the peptide sequences obtained from the purified protein. Attempts to extend this sequence to the 5'-end by the use of a primer extension library and 5'-RACE only succeeded in adding about 200 nt to this sequence without identification of the start codon. A partial length rat cDNA was then used to screen a human fetal liver library, which did yield the full-length clone depicted in SEQ ID NO: 63. This clone contains a deduced amino acid sequence (SEQ ID NO: 64) corresponding to all of 22 independent (some overlapping) peptide sequences obtained from the purified rat and porcine liver AMPK γ, confirming clonal identity.

A typical Kozak translation initiation sequence surrounds the assigned methionine start codon; this start is also in-frame with a 5'-upstream stop codon. The assigned start methionine is followed by an open reading frame predicting a protein of 331 amino acids and of 37,546 Da, which corresponds to the molecular weight observed on SDS gel electrophoresis of the protein as purified from rat and porcine liver. Expression of a truncated rat AMPK γ cDNA (aa residues 33–331) and the full-length human AMPK γ (331 aa) in COS7 cells yields products consistent with the molecular weight predicted for each cDNA (34,081 and 37,577 daltons, respectively). The rat liver AMPK γ product expressed in bacteria also displayed the molecular weight predicted by the cDNA. Thus, unlike AMPK β, there is no anomalous migration of the protein product of AMPK γ cDNA.

Comparison of the human and rat liver AMPK γ amino acid sequences to the database yields a significant alignment of this protein with the *S. cerevisiae* Snf4p. In addition, human full-length cDNA of the present invention also aligns with several other human partial length EST-cDNA sequences from brain, breast, placenta, liver and heart, recently reported in the database. Inspection of these sequences reveals that there are multiple isoforms of the human AMPK γ protein. There are likely also similar AMPK γ isoform families expressed in the rat and pig. This latter expectation is based on sequence analysis of 14 other MOPAC-derived partial AMPK γ cDNA sequences, as identified on colony hybridization of the AMPK γ MOPAC products with ³²P-labeled degenerate oligonucleotides. These products showed at least two reproducible patterns of nucleotide heterogeneity within the non-degenerate core.

Rat and human liver AMPK γ is a mammalian homolog of the *S. cerevisiase* Snf4p (CAT3) (Celenza et al. (1989) *Mol. Cell. Biol.,* 9, 5045–5054; Schuller, H. J. and Entian, K. D. (1988) *Gene,* 67, 247–257; Fields, S. and Song, O. K.

(1989) *Nature,* 340, 245–246). Snf4p was shown to interact with the Snf1p protein in the first reported use of the 2-hybrid system and also co-immunoprecipitates with it (Haygood, M. G. (1993) *Biotechniques* 15, 1084–1089). Indeed, on isolation of the Snf1p kinase from yeast, Snf4p, but not the other Snf1p-interacting proteins, co-purifies in a 1:1 stoichiometry with the Snf1p polypeptide. Analysis of SNF4 mutants in yeast suggests that Snf4p also positively regulates the activity of its associated catalytic subunit, Snf1p. By analogy, our prediction is that AMPK γ will also have such a positive influence on the AMPK α subunit.

Examination of the database reveals that, in addition to the homology of AMPK γ to Snf4p, there are 2 or 3 different human proteins highly homologous or identical to our human and rat liver AMPK γ sequences. However, some of these database sequences, as predicted from EST-cDNAs in brain, heart, breast and placenta, are distinct from each other and from our clones; some, for example, have a C-terminal extension. This indicates that there is a mammalian isoform family of potential AMPK γ subunits, each perhaps with different tissue expression and regulatory roles. It is suggests that these different gamma isoforms be designated $\gamma_1$, $\gamma_2$, $\gamma_3 \ldots \gamma_n$, as their full-length sequences are delineated. The rat liver/human liver AMPK γ sequence of the present invention is designated herein as AMPK $\gamma_1$.

AMPK α catalytic unit is widely expressed in several rat tissues. AMPK β and AMPK γ sequences have a similar wide tissue expression. Two species of AMPK γ mRNA of 2.7 and 1.9 kb are evident in total mRNA preparations; only the latter is present in polyA+-RNA from rat liver, suggesting that the larger mRNA is an unprocessed precursor. Only a single mRNA species for AMPK β of 1.9 kb is evident. Both AMPK γ and AMPK β mRNAs are highly expressed in kidney, white adipose tissue, lung and spleen, while AMPK γ mRNA appears to be more highly expressed in heart and brain. While detectable, the mRNA level for each subunit is relatively lower in skeletal muscle, lactating mammary gland and liver. In other studies, high concentrations of mRNA have been found for both subunits in the rat Fao hepatoma cell and the Syrian hamster insulin-secreting HIT cell, cell lines that both express substantial levels of AMPK activity.

AMPK was first recognized as a protein kinase active on enzymes of lipid metabolism (acetyl-CoA carboxylase, HMG Co-A reductase and hormone-sensitive lipase). However, as has been observed for the AMPK α subunit, the AMPK β and AMPK $\gamma_1$ subunits have wider tissue distribution than might be expected for a protein active only in the regulation of lipid metabolism. While mRNAs for each are detectable in "classic" lipogenic tissues like liver, white adipose tissue and lactating mammary gland, high concentrations of mRNA in non-lipogenic tissues like heart, brain, spleen and lung, for example, suggest that these proteins have roles that extend beyond the regulation of biosynthesis of fatty acids and sterols and fatty acid oxidation.

For example, the striking homology of all three subunits to yeast proteins that are involved in nutrient (glucose) responses suggests that the three mammalian proteins may be involved in glucose (or other nutrient) regulation of gene expression in mammalian tissues or in other adaptive responses to a changing nutrient environment. In addition, AMPK may be a important "metabolic sensor" linked to oxidative fuel choice in the heart and to glucose sensing in the pancreatic beta cell, perhaps being important for insulin secretion.

The following nonlimiting examples are provided to further illustrate the instant invention.

EXAMPLES

Example 1

Purification of AMPK Catalytic Subunit (α1)

Enzyme Purification

AMPK was purified from porcine liver. Liver (1 kg) was homogenized in 4,000 ml of buffer. A 2.5–7.0% (w/v) PEG 6000 fraction was prepared and the resultant fraction batched onto 1,500 ml of DEAE cellulose (Whatman, Clifton, N.J.) and eluted with buffer containing 0.25 M NaCl (2,000 ml). The eluate was chromatographed on 150 ml Blue Sepharose (Pharmacia, Uppsala, Sweden) and the AMPK eluted with buffer containing 1 M NaCl. The enzyme fraction was concentrated and desalted by 10% (w/v) PEG-6000 precipitation prior to chromatography by peptide substrate affinity chromatography. The peptide substrate affinity column was washed with the same buffer containing 0.1% (v/v) Triton X-100 and 0.5 M NaCl and the AMPK eluted with this buffer containing 2 M NaCl and 30% (v/v) ethylene glycol.

Protein Kinase Assays

The AMPK was assayed in accordance with procedures described by Davies et al. (1989) *Eur. J. Biochem.* 186, 123–128 using the SAMS peptide substrate, HMRSAMSGLHLVKRR-amide (SEQ ID NO: 49). The enzyme was diluted in diluting buffer (20 mM HEPES pH 7.0, 0.1% (v/v) Triton X-100) prior to assay and the reactions were initiated by adding 10 ml diluted enzyme to the reaction mixture containing peptide substrate. The reactions were stopped by withdrawing 30 ml aliquots and applying to P81 papers in accordance with procedures described by Pearson, R. B., Mitchelhill, K. I., and Kemp, B. E. (1993) in *Protein Phosphorylation: A Practical Approach*, Hardie, G. D. (ed) Oxford University Press, pp 265–291.

Peptide Synthesis

Peptides were synthesized using an Applied Biosystems 430 synthesizer in accordance with procedures described by Pearson, R. B., Mittchelhill, K. I., and Kemp, B. E. (1993) in *Protein Phosphorylation: A Practical Approach,* Hardie, G. D. (ed) Oxford University Press, pp 265–291. All peptides were purified by cation-exchange chromatography followed by reverse phase chromatography. Peptides were analyzed by quantitative amino acid analysis using a Beckman 6300 amino acid analyzer. The peptide substrate affinity column was prepared by coupling the ADR1(222–234)$^{P229}$, peptide to a Pharmacia HiTrap N-hydroxysuccinamide ester activated superose column. This resin contains a 6-aminohexanoic acid spacer arm. The conditions of coupling were performed in accordance with manufacturer's instructions with 10 mg peptide per 5 ml column and peptide coupling was monitored by reverse phase HPLC.

Example 2

Isolation of cDNA Encoding AMPK Catalytic Subunit (α1)

Peptide Sequencing

Peptides were derived from rat and porcine α1 subunit of the AMPK, by in situ proteolysis in accordance with procedures described by Mitchelhill et al. (1994) *J. Biol. Chem.* 269, 2361–2364 and sequenced on either an Applied Biosystems 471A Protein Sequencer or a Hewlett Packard G1000A Protein Sequencer.

Tissue Distribution Activity Studies

A 35% saturated ammonium sulfate fraction was prepared for each tissue, following homogenization in AMPK homogenization buffer (HB, 50 mM Tris-HCl pH 8.5, 250 mM sucrose, 5 mM sodium pyrophosphate, 50 mM sodium fluoride, 1 mM EGTA, 1 mM EDTA, 1 mM DTT, 1 mM benzamidine, 1 μg/ml soybean trypsin inhibitor and 0.2 mM phenylmethyl-sulfonylfluoride). The resultant pellet was resuspended in 5 ml HB and assayed for protein concentration. The AMPK was assayed in accordance with procedures described by Mitchelhill et al. (1994) *J. Biol. Chem.* 269, 2361–2364 with the following modifications: a final reaction volume of 120 μl was used, enzyme aliquots (30 μl) containing 1 μg protein pre-diluted in 50 mM Tris-HCl pH 7.5 and 0.05% (v/v) Triton X-100 were used to initiate the reaction. Three aliquots (30 μl) were removed after 2, 4 and 6 min. Reactions were performed in duplicate ±5'-AMP (200 μM), with a minus peptide substrate control. The specific activity of the enzyme was determined using linear rates of phosphorylation with the specific synthetic peptide substrate SAMS. The AMPK was purified from rat or porcine liver as described in Example 1 using substrate affinity chromatography.

Isolation of AMPK cDNA

A radiolabelled cDNA (774 bp) encoding porcine AMPK $\alpha_1$ was used to screen a rat hypothalamus Zap II cDNA library (Stratagene, La Jolla, Calif.) according to the manufacturer's instructions. Positives were plaque-purified on subsequent rounds of screening and phagemid from positive clones were rescued with helper phage (Stratagene). Screening of 7×10$^6$ plaques yielded three unique clones, the largest consisting of an open reading frame, corresponding to AMPK $\alpha_1$ (2–549).

The AMPK $\alpha_1$ 5' end was isolated using a Gibco 5'-RACE kit (Life Technologies, Grand Island, USA) with an $\alpha_1$ specific primer to residues 41–48 and rat liver cDNA. Human AMPK $\alpha_1$ (14–270) was isolated from fetal human liver cDNA primed with sense and anti-sense partially degenerate oligonucleotides to $\alpha_1$ peptide sequence by RT-PCR. Human AMPK $\alpha_1$, residues 291–448 is a partial length human liver cDNA clone obtained from the Lawrence Livermore National Laboratory (clone 78297, accession number T50799).

Northern Blotting

A rat multiple tissue Northern (MTN) blot (Clontech, Palo Alto, Calif., USA) containing 2 mg of poly(A)+ RNA of individual tissues was probed with $^{32}$P-labelled rat AMPK $\alpha_1$ and $\alpha_2$ cDNAs according to the instructions supplied.

Production of Anti-AMPK Antibodies

Polyclonal antibodies to AMPK $\alpha_1$ and $\alpha_2$ were prepared as follows. Peptides based on the predicted amino acid sequences of AMPK $\alpha_1$ for residues 339–358 (DFYLATSPPDSFLDDHHLTR (SEQ ID NO: 50)) and AMPK $\alpha_2$ for residues 352–366 (MDDSAMHIPPGLKPH (SEQ ID NO: 51)) were synthesized and coupled to keyhole limpet hemocyanin (Sigma Chemical Co. St. Louis, Mo., H-2133) via a cysteine residue added to the N-terminus of the peptide using the heterobifunctional reagent, N-succinimidyl-3-(2-pyridyldithio)propionate (Pharmacia, Uppsala, Sweden). New Zealand White rabbits were immunized with 2 mg peptide conjugate initially in 50% (v/v) Freund's complete adjuvant and in 50% (v/v) Freund's incomplete adjuvant for subsequent immunizations. Rabbits were boosted fortnightly with 2 mg peptide conjugate and bled 7 days after booster injections. Anti-AMPK $\alpha_1$ and $\alpha_2$ peptide antibodies were purified by peptide affinity chromatography.

Western Blotting

Multiple rat tissue western blots were prepared as follows. Rat tissues were homogenized in AMPK HB and a 2.5–7% polyethylene glycol 6000 fraction was prepared. The resultant pellet was resuspended in 5 ml HB and assayed for protein concentration. One hundred micrograms of each tissue fraction was analyzed by SDS PAGE (13% acrylamide gels); transferred to nitrocellulose (Schleicher & Schuell, Dassal, Germany); and probed with 3 μg/ml and 6 μg/ml affinity purified AMPK $\alpha_1$ and $\alpha_2$ antibodies, respectively. Primary antibody was detected using anti-rabbit IgG antibody conjugated to horseradish peroxidase (DAKO, Carpinteria, Calif., USA) and 0.032% 3,3'-diaminobenzidine (D-5637, Sigma) together with 0.064% $H_2O_2$.

Purification of AMPK $\alpha_2$

Affinity purified AMPK $\alpha_2$ antibody (2 mg) was coupled to CNBr-activated Sepharose 4B (Pharmacia, Uppsala, Sweden) according to the manufacturer's instructions. The unbound fraction from the substrate affinity column was applied directly to the AMPK $\alpha_2$ antibody column, washed with 5 volumes of PBS and eluted with 200 mM glycine buffer pH 2.5 and immediately neutralized.

Example 3

Isolation of cDNAs Encoding AMPK Non-Catalytic Subunits

AMPK Isolation and Peptide Sequencing

Porcine and rat liver AMPK was isolated. Peptide sequences derived from the rat liver beta (40 kDa) and gamma (38 kDa) subunits were obtained after subunit separation by SDS gel electrophoresis, band elution and in situ protease digestion in accordance with procedures described by Mitchelhill et al. (1994) *J. Biol. Chem.* 269, 2361–2364 and Stapleton et al. (1994) *J. Biol. Chem.* 269, 29343–29346.

AMPK β Subunit cDNA Isolation

Peptide sequences derived from the AMPK β subunit were used to generate partial length AMPK β subunit cDNAs by the polymerase chain reaction (PCR) in accordance with procedures described by Gao et al. (1995) *Biochem. Biophys. Acta.* 1200, 73–82. One product, a 309 bp cDNA, was used to screen a rat liver λZAPII cDNA library (Stratagene). Filters were hybridized with $^{32}$P-cDNA, labelled with alpha-$^{32}$P-CTP (3000 mCi/mmol, New England Nuclear) by random priming (Random Primer cDNA Labeling System, Gibco/BRL), in 50% formamide, 10×Denhardt's, 1M NaCl, 50 mM Tris-Cl (pH 7.5), and 100 μg/ml salmon sperm DNA at 42° C. for 18 hours. They were then washed at room temperature 3×10 minutes and then at 55° C. for 15 minutes. Autoradiography was for overnight at −80° C. All plates were lifted in duplicate and positive plaques were purified through 3 additional rounds of plating and re-screening.

AMPK γ Subunit cDNA Isolation

Where peptide sequences are listed herein, the letters Y,H,N and R indicate regions of degeneracy. For the AMPK γ subunit, a 67 bp cDNA was generated by the MOPAC technique described by Lee, C. C. and Caskey, C. T., (1990) in *PCR Protocols,* (Innis, M. A. Gelfand, D. H., Srinsky, J. J., and White, T. J. editors), pp. 46–53, Academic Press, Inc., London. Degenerate PCR primers were synthesized corresponding to the N-and C- terminal sequences of a 17-amino acid rat liver AMPK γ peptide (VVDIYSKFDVINLAAEK (SEQ ID NO: 52). The sequence of the sense primer was GCGGATCCGTNGAYATHTA (SEQ ID NO: 53) and the sequence of the antisense primer was CGGAATTCYT-TYTCNGCNGCNA (SEQ ID NO: 54). BamHI and EcoRI sites were added to the 5'-ends of these primers. The strategy was to create a non-degenerate nucleotide sequence corresponding to the middle portion of the peptide sequence that would be used in library screening. Total rat liver cDNA, prepared with oligo-dT and random hexamers (GIBCO/BRL pre-amplification kit), was used with PCR to amplify a 67-mer (including primers) oligonucleotide corresponding to a portion of the AMPK γ cDNA. The purified PCR product was digested with BamHI and EcoRI and ligated into peluescript plasmid for transformation of DH5α bacteria. Colony hybridization was employed to identify clones of interest; colonies were lifted from replica plates onto nitrocellulose filters. Following bacterial lysis and DNA denaturation, filters were probed with a mixture of two $^{32}$P-end-labeled degenerate oligonucleotide probes corresponding to amino acid sequence (KFDVINLA (SEQ ID NO: 55)) internal to that of the two PCR primers. These oligonucleotides (#1: AARTTYGAYGTNATHAAYCT-NGC (SEQ ID NO: 56); #2: AARTTYGAYGTNATHAAY-TTRGC SEQ ID NO: 57)) were added in a ratio of two parts oligo #1 to one part oligo #2 to reflect the degeneracy of the Leu codon. Positive colonies were identified and plasmid DNA isolated from each for sequence analysis. One such cDNA was chosen and the non-degenerate "core" 23-mer oligonucleotide sequence was then synthesized for use in library screening (CTCCAAGTTTGATGTTATCAACC (SEQ ID NO: 58)). Screening of approximately $10^6$ plaques with this probe, however, did not yield any positive clones.

The non-degenerate 23-mer cDNA was then used in conjugation with degenerate primers constructed from two other peptide sequences to generate a larger AMPK γ cDNA by PCR. Both sense and antisense degenerate oligonucleotide primers corresponding to the peptide sequences, EEL-QIG (SEQ ID NO: 59) and FPKPEFM (SEQ ID NO: 60), were used together with the sense MOPAC-derived non-degenerate sequence to generate all possible PCR products, using rat liver cDNA as template. The largest product (192 bp) obtained was subcloned in pCR-Script (Stratagene) and sequenced. This sequence, which actually had a predicted amino acid sequence corresponding to all three AMPK γ peptides used in the PCR strategy, was then used for library screening, as above. Screening of $2\times10^6$ plaques with this larger PCR product yielded several positive clones; however, none of the rat cDNAs (1–1.3 kb) isolated corresponded to a full-length open reading frame. In an effort to extend the sequence to the 5'-end of the ORF, a primer extension library was constructed using a AMPK γ-specific antisense primer (Stratagene; λZAPII). Additional screening of this library, while yielding some 5'-extended sequence, did not yield the start Met codon. The application of a 5'-RACE strategy with rat liver cDNA was also unsuccessful in attempts at sequence extension, although a 5'-RACE product from porcine liver was obtained. The most 5'rat cDNA sequence (520 bp) was then used to screen a human fetal liver library, which yielded a full-length AMPK γ cDNA.

Plasmid Preparation and DNA Sequencing

Plasmid DNA was prepared using Qiagen Mini- or Midi-columns (Chatsworth, Calif.) according to the manufacturer's instructions. DNA was sequenced, with vector or gene-specific primers, using an Applied Biosystems Prism(tm) (Foster City, Calif.) ready reaction Dye Deoxy Terminator Cycle Sequencing kit, and cycled in a Perkin-Elmer PCR Thermocycler, according to the manufacturers' instructions. Dye terminators were removed from the resulting sequence reactions using a Centri-Step column (Princeton Separations, Inc.). The purified sequencing reactions were then dried in a Speed-Vac and analyzed on an automated DNA sequencer (Applied Biosystems Model 373).

Bacterial Expression of cDNAs

Full-length rat AMPK β subunit cDNA and a partial length rat AMPK γ (aa 33–331) subunit cDNA were expressed in *E. coli* using the pET vector system, which introduces polyhistidine (His6) and T7 fusion epitope tag sequences (Novagen, Madison, Wis.). Bacterial expression was induced with 1.0 mM IPTG at 37° C. for 2 hours. Expressed protein was detected by both Coomassie blue staining and immunoblotting with anti-T7 monoclonal antibody (Novagen). The fusion proteins were purified from the inclusion bodies of bacteria by nickel affinity chromatography under denaturing conditions. His6-AMPK β or His6-AMPK γ were solubilized from the inclusion bodies in 6 M urea, according to manufacturer's instructions. After sample application, the column was washed extensively with Tris-Cl (20 mM; pH 7.9), 0.5 M NaCl (0.5 M), imidazole (20 mM) and urea (6 M). The His6-protein was eluted with the same buffer containing 300 mM imidazole.

Cellular Expression of cDNAs

Full-length rat AMPK β cDNA, a partial length rat AMPK γ (aa 33–331) and full-length human AMPK γ subunit cDNAs were also expressed in COS7 cells. cDNAs were cloned into a pMT2 vector in-frame with a hemagglutinin (HA) epitope tag (pMT2-HA). Transfection was done using Lipofectamine reagent (Gibco/BRL), according to the manufacturer's general protocol. Cells were plated at $3\times10^5$/ well in 6 well plates in DMEM containing 10% fetal calf serum and penicillin/streptomycin. The following day, the cells were switched to serum-free, antibiotic-free DMEM and then lipofectamine-DNA conjugates (2 μg of DNA; 10 μl lipofectamine per well) diluted in the same medium were added. After 5 hours incubation at 37° C., an equal volume of medium containing 20% fetal calf serum was added to each well. The following morning, the medium was switched to the original cell medium. Cells were harvested 48 hours after transfection. After washing with PBS, cells were lysed in a buffer containing Tris-Cl (50 mM; pH 7.5), NaCl (100 mM), NaF (50 mM), NaPP$_i$ (5 mM), EDTA (1 mM), DTT (2 mM) and NP-40 (0.5%) with several protease inhibitors.

For complete lysis, cells were placed on ice for 15 minutes followed by scraping and vigorous vortexing (15 seconds) of the lysate. After clearing of debris by brief centrifugation, this lysate was used for SDS gel electrophoresis and immunoblotting. Blots were probed with an anti-HA monoclonal antibody (derived from the 12CA5 hybridoma line). After secondary probing with an anti-mouse IgG-peroxidase antibody, blots were developed by ECL (Amersham).

Northern Blot Analysis

Total RNA was isolated from the tissues of male Sprague-Dawley rats (150–200 grams body weight; Charles River) or from the lactating mammary gland of female rats using a guanidium isothiocyanate-lithium chloride method. RNAs were fractionated on 1% agarose/formaldehyde gels with capillary transfer to nitrocellulose (MSI). cDNA probes were labelled by random priming.

Hybridization was carried in 5×Denhardt's, 0.2 M Tris (pH 7.4), 1M NaCl and 0.1 mg/ml salmon sperm DNA at 42° C. for 20 hours. Filters were washed sequentially with 2×SSPE/0.1% SDS (room temperature; 2×15 minutes), 0.2× SSPE/0.1% SDS (room temperature; 2×15 minutes) and with 0.2×SSPE/0.1% SDS (55° C.; 2×15 minutes). Autoradiography on Kodak XAR film with enhancing screens was at −80° C. for 18–48 hours.

DNA Sequence Analysis and DNA Sequences

DNA sequences were analyzed using MacVector (r) and the GCG software package. Sequences were compared to the data base using BLAST and GCG; amino acid alignments were made using the Pileup program of GCG. Sequences were formatted using an Excel(r) macro. The DNA sequences described herein have been deposited in the GenBank with the following accession numbers: rat liver AMPK β (U42411), rat liver AMPK γ (U42413) and human fetal liver AMPK γ (U42412).

What is claimed is:

1. An isolated, purified nucleic acid sequence encoding mammalian AMPK $\alpha_1$ comprising SEQ ID NO: 44.

2. A vector comprising a nucleic acid sequence of claim 1.

3. A host cell comprising a vector of claim 2.

4. A method of producing mammalian AMPK $\alpha_1$ comprising:
   (a) culturing cells of claim 3 under conditions which allow expression of the nucleic acid sequence encoding mammalian AMPK $\alpha_1$; and
   (b) recovering the expressed AMPK $\alpha_1$ from the cell.

5. An isolated, purified nucleic acid sequence encoding mammalian AMPK $\beta$, said nucleic acid sequence comprising SEQ ID NO: 61.

6. A vector comprising the nucleic acid sequence of claim 5.

7. A host cell comprising a vector of claim 6.

8. A recombinant AMPK $\beta$ polypeptide encoded by the nucleic acid sequence of claim 5.

9. A method of producing mammalian AMPK $\beta$ comprising:
   (a) culturing cells of claim 7 under conditions which allow expression of the nucleic acid sequence encoding AMPK $\beta$; and
   (b) recovering the expressed AMPK $\beta$.

10. A substantially purified polypeptide comprising an amino acid sequence of SEQ ID NO: 62.

11. An isolated, purified nucleic acid sequence encoding mammalian AMPK $\gamma$, said nucleic acid sequence comprising SEQ ID NO: 63.

12. A vector comprising the nucleic acid sequence of claim 11.

13. A host cell comprising a vector of claim 12.

14. A recombinant AMPK $\gamma$ polypeptide encoded by the nucleic acid sequence of claim 11.

15. A method of producing mammalian AMPK $\gamma$ comprising:
   (a) culturing cells of claim 13 under conditions which allow expression of the nucleic acid sequence encoding AMPK $\gamma$; and
   (b) recovering the expressed AMPK $\gamma$.

16. A substantially purified polypeptide comprising an amino acid sequence of SEQ ID NO: 64.

* * * * *

UNITED STATES PATENT AND TRADEMARK OFFICE
CERTIFICATE OF CORRECTION

PATENT NO. : 6,124,125
DATED : September 26, 2000
INVENTOR(S) : Kemp, et al.

It is certified that error appears in the above-identified patent and that said Letters Patent is hereby corrected as shown below:

At col 15, line 6, please delete "peluescript" and insert therefor --pBluescript--

Signed and Sealed this

First Day of May, 2001

Attest:

NICHOLAS P. GODICI

Attesting Officer

Acting Director of the United States Patent and Trademark Office

```
                            SEQUENCE LISTING (1) GENERAL INFORMATION:

(iii) NUMBER OF SEQUENCES:  64

(2) INFORMATION FOR SEQ ID NO: 1:

(i) SEQUENCE CHARACTERISTICS:
          (A) LENGTH:  345
          (B) TYPE:  Amino acid
          (D) TOPOLOGY: Linear (xi) SEQUENCE DESCRIPTION:   SEQ ID NO: 1:

Met Ala Glu Lys Gln Lys His Gly Arg Val Lys Ile Gly His Tyr
1               5                   10                  15

Ile Leu Gly Asp Thr Leu Gly Val Gly Thr Phe Gly Lys Val Lys
                20                  25                  30

Val Gly Lys His Glu Leu Thr Gly His Lys Val Ala Val Lys Ile
                35                  40                  45

Leu Asn Arg Gln Lys Ile Arg Leu Asp Val Val Gly Lys Ile Arg
                50                  55                  60

Arg Glu Ile Gln Asn Leu Lys Leu Phe Arg His Pro His Ile Ile
                65                  70                  75

Lys Leu Tyr Gln Val Ile Ser Thr Pro Ser Asp Ile Phe Met Val
                80                  85                  90

Met Glu Tyr Val Ser Gly Gly Glu Leu Phe Asp Tyr Ile Cys Lys
                95                  100                 105

Asn Gly Arg Leu Asp Glu Lys Glu Ser Arg Arg Leu Phe Gln Gln
                110                 115                 120

Ile Leu Ser Gly Val Asp Tyr Cys His Arg His Met Val Val His
                125                 130                 135

Arg Asp Leu Lys Pro Glu Asn Val Leu Leu Asp Ala His Met Asn
                140                 145                 150

Ala Lys Ile Ala Asp Phe Gly Leu Ser Asn Met Met Ser Asp Gly
                155                 160                 165

Glu Phe Leu Arg Thr Ser Cys Gly Ser Pro Asn Tyr Ala Ala Pro
                170                 175                 180

Glu Val Ile Ser Gly Arg Leu Tyr Ala Gly Pro Glu Val Asp Ile
                185                 190                 195

Trp Ser Ser Gly Val Ile Leu Tyr Ala Leu Leu Cys Gly Thr Leu
                200                 205                 210

Pro Phe Asp Asp Asp His Val Pro Thr Leu Phe Lys Lys Ile Cys
                215                 220                 225

Asp Gly Ile Phe Tyr Thr Pro Gln Tyr Leu Asn Pro Ser Val Ile
                230                 235                 240

Ser Leu Leu Lys His Met Leu Gln Val Asp Pro Met Lys Arg Ala
                245                 250                 255

Thr Ile Lys Asp Ile Arg Glu His Glu Trp Phe Lys Gln Asp Leu
                260                 265                 270

Pro Lys Tyr Leu Phe Pro Glu Asp Pro Ser Tyr Ser Ser Thr Met
```

```
                275                 280                 285
Ile Asp Asp Glu Ala Leu Lys Glu Val Cys Glu Lys Phe Glu Cys
                290                 295                 300

Ser Glu Glu Glu Val Leu Ser Cys Leu Tyr Asn Arg Asn His Gln
                305                 310                 315

Asp Pro Leu Ala Val Ala Tyr His Leu Ile Ile Asp Asn Arg Arg
                320                 325                 330

Ile Met Asn Glu Ala Lys Asp Phe Tyr Leu Ala Thr Ser Pro Pro
                335                 340                 345

(2) INFORMATION FOR SEQ ID NO: 2:

(i) SEQUENCE CHARACTERISTICS:
        (A) LENGTH:  11
        (B) TYPE:  Amino acid
        (D) TOPOLOGY: Linear (xi) SEQUENCE DESCRIPTION:  SEQ ID NO: 2:

Asp Ser Phe Leu Asp Asp His His Leu Thr Arg
1               5                   10

(2) INFORMATION FOR SEQ ID NO: 3:

(i) SEQUENCE CHARACTERISTICS:
        (A) LENGTH:  56
        (B) TYPE:  Amino acid
        (D) TOPOLOGY: Linear (xi) SEQUENCE DESCRIPTION:  SEQ ID NO: 3:

Pro His Pro Glu Arg Val Pro Phe Leu Val Ala Glu Thr Pro Arg
1               5                   10                  15

Ala Arg His Thr Leu Asp Glu Leu Asn Pro Gln Lys Ser Lys His
                20                  25                  30

Gln Gly Val Arg Lys Ala Lys Trp His Leu Gly Ile Arg Ser Gln
                35                  40                  45

Ser Arg Pro Asn Asp Ile Met Ala Glu Val Cys
                50                  55

(2) INFORMATION FOR SEQ ID NO: 4:

(i) SEQUENCE CHARACTERISTICS:
        (A) LENGTH:  70
        (B) TYPE:  Amino acid
        (D) TOPOLOGY: Linear (xi) SEQUENCE DESCRIPTION:  SEQ ID NO: 4:

Arg Ala Ile Lys Gln Leu Asp Tyr Glu Trp Lys Val Val Asn Pro
1               5                   10                  15

Tyr Tyr Leu Arg Val Arg Arg Lys Asn Pro Val Thr Ser Thr Phe
                20                  25                  30

Ser Lys Met Ser Leu Gln Leu Tyr Gln Val Asp Ser Arg Thr Tyr
                35                  40                  45

Leu Leu Asp Phe Arg Ser Ile Asp Asp Glu Ile Thr Glu Ala Lys
                50                  55                  60

Ser Gly Thr Ala Thr Pro Gln Arg Ser Gly
                67                  70

(2) INFORMATION FOR SEQ ID NO: 5:

(i) SEQUENCE CHARACTERISTICS:
        (A) LENGTH:  64
```

(B) TYPE:  Amino acid
        (D) TOPOLOGY: Linear (xi) SEQUENCE DESCRIPTION:  SEQ ID NO: 5:

Ser Ile Ser Asn Tyr Arg Ser Cys Gln Arg Ser Asp Ser Asp Ala
1               5                  10                  15

Glu Ala Gln Gly Lys Pro Ser Glu Val Ser Leu Thr Ser Ser Val
               20                  25                  30

Thr Ser Leu Asp Ser Ser Pro Val Asp Val Ala Pro Arg Pro Gly
               35                  40                  45

Ser His Thr Ile Glu Phe Phe Glu Met Cys Ala Asn Leu Ile Lys
               50                  55                  60

Ile Leu Ala Gln (2) INFORMATION FOR SEQ ID NO: 6:

(i) SEQUENCE CHARACTERISTICS:
        (A) LENGTH:  257
        (B) TYPE:  Amino acid
        (D) TOPOLOGY: Linear (xi) SEQUENCE DESCRIPTION:  SEQ ID NO: 6:

Gly His Tyr Ile Leu Gly Asp Thr Leu Gly Val Gly Thr Phe Gly
1               5                  10                  15

Lys Val Lys Val Gly Lys His Glu Leu Thr Gly His Lys Val Ala
               20                  25                  30

Val Lys Ile Leu Asn Arg Gln Lys Ile Arg Ser Leu Asp Val Val
               35                  40                  45

Gly Lys Ile Arg Arg Glu Ile Gln Asn Leu Lys Leu Phe Arg His
               50                  55                  60

Pro His Ile Ile Lys Leu Tyr Gln Val Ile Ser Thr Pro Ser Asp
               65                  70                  75

Ile Phe Met Val Met Glu Tyr Val Ser Gly Gly Glu Leu Phe Asp
               80                  85                  90

Tyr Ile Cys Lys Asn Gly Arg Leu Asp Glu Lys Glu Ser Arg Arg
               95                 100                 105

Leu Phe Gln Gln Ile Leu Ser Gly Val Asp Tyr Cys His Arg His
              110                 115                 120

Met Val Val His Arg Asp Leu Lys Pro Glu Asn Val Leu Leu Asp
              125                 130                 135

Ala His Met Asn Ala Lys Ile Ala Asp Phe Gly Leu Ser Asn Met
              140                 145                 150

Met Ser Asp Gly Glu Phe Leu Arg Thr Ser Cys Gly Ser Pro Asn
              155                 160                 165

Tyr Ala Ala Pro Glu Val Ile Ser Gly Arg Leu Tyr Ala Gly Pro
              170                 175                 180

Glu Val Asp Ile Trp Ser Ser Gly Val Ile Leu Tyr Ala Leu Leu
              185                 190                 195

Cys Gly Thr Leu Pro Phe Asp Asp His Val Pro Thr Leu Phe
              200                 205                 210

Lys Lys Ile Cys Asp Gly Ile Phe Tyr Thr Pro Gln Tyr Leu Asn
              215                 220                 225

Pro Ser Val Ile Ser Leu Leu Lys His Met Leu Gln Val Asp Pro
              230                 235                 240

Met Lys Arg Ala Thr Ile Lys Asp Ile Arg Glu His Glu Trp Phe
              245                 250                 255

Lys Gln (2) INFORMATION FOR SEQ ID NO: 7:

(i) SEQUENCE CHARACTERISTICS:
        (A) LENGTH: 55
        (B) TYPE: Amino acid
        (D) TOPOLOGY: Linear (xi) SEQUENCE DESCRIPTION: SEQ ID NO: 7:

```
Glu Ala Leu Lys Glu Val Cys Glu Lys Phe Glu Cys Ser Glu Glu
1               5                   10                  15

Glu Val Leu Ser Cys Leu Tyr Asn Arg Asn His Gln Asp Pro Leu
                20                  25                  30

Ala Val Ala Tyr His Leu Ile Ile Asp Asn Arg Arg Ile Met Asn
                35                  40                  45

Glu Ala Lys Asp Phe Tyr Leu Ala Thr Ser
                50                  55
```

(2) INFORMATION FOR SEQ ID NO: 8:

(i) SEQUENCE CHARACTERISTICS:
        (A) LENGTH: 9
        (B) TYPE: Amino acid
        (D) TOPOLOGY: Linear (xi) SEQUENCE DESCRIPTION: SEQ ID NO: 8:

```
Phe Leu Asp Asp His His Leu Thr Arg
1               5
```

(2) INFORMATION FOR SEQ ID NO: 9:

(i) SEQUENCE CHARACTERISTICS:
        (A) LENGTH: 56
        (B) TYPE: Amino acid
        (D) TOPOLOGY: Linear (xi) SEQUENCE DESCRIPTION: SEQ ID NO: 9:

```
Pro His Pro Glu Arg Val Pro Phe Leu Val Ala Glu Thr Pro Arg
1               5                   10                  15

Ala Arg His Thr Leu Asp Glu Leu Asn Pro Gln Lys Ser Lys His
                20                  25                  30

Gln Gly Val Arg Lys Ala Lys Trp His Leu Gly Ile Arg Ser Gln
                35                  40                  45

Ser Arg Pro Asn Asp Ile Met Ala Glu Val Cys
                50                  55
```

(2) INFORMATION FOR SEQ ID NO: 10:

(i) SEQUENCE CHARACTERISTICS:
        (A) LENGTH: 10
        (B) TYPE: Amino acid
        (D) TOPOLOGY: Linear (xi) SEQUENCE DESCRIPTION: SEQ ID NO: 10:

```
Arg Pro Asn Asp Ile Met Ala Glu Val Cys
1               5                   10
```

(2) INFORMATION FOR SEQ ID NO: 11:

(i) SEQUENCE CHARACTERISTICS:
        (A) LENGTH: 70
        (B) TYPE: Amino acid (D) TOPOLOGY: Linear (xi) SEQUENCE DESCRIPTION: SEQ ID NO: 11:

Arg Ala Ile Lys Gln Leu Asp Tyr Glu Trp Lys Val Val Asn Pro
1               5                   10                  15

Tyr Tyr Leu Arg Val Arg Arg Lys Asn Pro Val Thr Ser Thr Tyr
                20                  25                  30

Ser Lys Met Ser Leu Gln Leu Tyr Gln Val Asp Ser Arg Thr Tyr
                35                  40                  45

Leu Leu Asp Phe Arg Ser Ile Asp Asp Glu Ile Thr Glu Ala Lys
                50                  55                  60

Ser Gly Thr Ala Thr Pro Gln Arg Ser Gly
                65                  70

(2) INFORMATION FOR SEQ ID NO: 12:

(i) SEQUENCE CHARACTERISTICS:
        (A) LENGTH: 64
        (B) TYPE: Amino acid
        (D) TOPOLOGY: Linear (xi) SEQUENCE DESCRIPTION: SEQ ID NO: 12:

Ser Val Ser Asn Tyr Arg Ser Cys Gln Arg Ser Asp Ser Asp Ala
1               5                   10                  15

Glu Ala Gln Gly Lys Ser Ser Glu Val Ser Leu Thr Ser Ser Val
                20                  25                  30

Thr Ser Leu Asp Ser Ser Pro Val Asp Leu Thr Pro Arg Pro Gly
                35                  40                  45

Ser His Thr Ile Glu Phe Phe Glu Met Cys Ala Asn Leu Ile Lys
                50                  55                  60

Ile Leu Ala Gln (2) INFORMATION FOR SEQ ID NO: 13:

(i) SEQUENCE CHARACTERISTICS:
        (A) LENGTH: 22
        (B) TYPE: Amino acid
        (D) TOPOLOGY: Linear (xi) SEQUENCE DESCRIPTION: SEQ ID NO: 13:

Asp Gly Arg Val Lys Ile Gly His Tyr Ile Leu Gly Asp Thr Leu
1               5                   10                  15

Gly Val Gly Thr Phe Gly Lys
                20

(2) INFORMATION FOR SEQ ID NO: 14:

(i) SEQUENCE CHARACTERISTICS:
        (A) LENGTH: 16
        (B) TYPE: Amino acid
        (D) TOPOLOGY: Linear (xi) SEQUENCE DESCRIPTION: SEQ ID NO: 14:

Asp Glu Lys Glu Ser Arg Arg Leu Phe Gln Gln Ile Leu Ser Gly
1               5                   10                  15

Val (2) INFORMATION FOR SEQ ID NO: 15:

(i) SEQUENCE CHARACTERISTICS:
        (A) LENGTH: 33

(B) TYPE: Amino acid
          (D) TOPOLOGY: Linear (xi) SEQUENCE DESCRIPTION: SEQ ID NO: 15:

Asp Leu Lys Pro Glu Asn Val Leu Leu Asp Ala His Met Asn Ala
1               5                  10                  15

Lys Ile Ala Asp Phe Gly Leu Ser Asn Met Met Ser Asp Gly Glu
                20                  25                  30

Phe Leu Arg (2) INFORMATION FOR SEQ ID NO: 16:

(i) SEQUENCE CHARACTERISTICS:
        (A) LENGTH: 13
        (B) TYPE: Amino acid
        (D) TOPOLOGY: Linear (xi) SEQUENCE DESCRIPTION: SEQ ID NO: 16:

Glu Val Ile Ser Gly Arg Leu Tyr Ala Gly Pro Glu Val
1               5                  10

(2) INFORMATION FOR SEQ ID NO: 17:

(i) SEQUENCE CHARACTERISTICS:
        (A) LENGTH: 9
        (B) TYPE: Amino acid
        (D) TOPOLOGY: Linear (xi) SEQUENCE DESCRIPTION: SEQ ID NO: 17:

Xaa Met Leu Gln Val Asp Pro Met Lys
1               5

(2) INFORMATION FOR SEQ ID NO: 18:

(i) SEQUENCE CHARACTERISTICS:
        (A) LENGTH: 35
        (B) TYPE: Amino acid
        (D) TOPOLOGY: Linear (xi) SEQUENCE DESCRIPTION: SEQ ID NO: 18:

Lys Asp Ile Arg Glu His Glu Xaa Phe Lys Gln Asp Leu Pro Lys
1               5                  10                  15

Tyr Leu Phe Pro Glu Asp Pro Ser Tyr Ser Xaa Thr Met Ile Asp
                20                  25                  30

Asp Glu Ala Leu Lys
                35

(2) INFORMATION FOR SEQ ID NO: 19:

(i) SEQUENCE CHARACTERISTICS:
        (A) LENGTH: 17
        (B) TYPE: Amino acid
        (D) TOPOLOGY: Linear (xi) SEQUENCE DESCRIPTION: SEQ ID NO: 19:

Xaa Xaa Gln Asp Pro Leu Ala Val Ala Tyr His Leu Ile Ile Asp
1               5                  10                  15

Asn Arg (2) INFORMATION FOR SEQ ID NO: 20:

(i) SEQUENCE CHARACTERISTICS:
        (A) LENGTH: 9
        (B) TYPE: Amino acid

```
            (D) TOPOLOGY: Linear (xi) SEQUENCE DESCRIPTION: SEQ ID NO: 20:

Asp Phe Tyr Leu Ala Thr Ser Pro Pro
1               5

(2) INFORMATION FOR SEQ ID NO: 21:

(i) SEQUENCE CHARACTERISTICS:
            (A) LENGTH: 11
            (B) TYPE: Amino acid
            (D) TOPOLOGY: Linear (xi) SEQUENCE DESCRIPTION: SEQ ID NO: 21:

Asp Ser Phe Leu Asp Asp His His Leu Thr Arg
1               5                   10

(2) INFORMATION FOR SEQ ID NO: 22:

(i) SEQUENCE CHARACTERISTICS:
            (A) LENGTH: 10
            (B) TYPE: Amino acid
            (D) TOPOLOGY: Linear (xi) SEQUENCE DESCRIPTION: SEQ ID NO: 22:

Val Pro Phe Leu Val Ala Glu Thr Pro Arg
1               5                   10

(2) INFORMATION FOR SEQ ID NO: 23:

(i) SEQUENCE CHARACTERISTICS:
            (A) LENGTH: 23
            (B) TYPE: Amino acid
            (D) TOPOLOGY: Linear (xi) SEQUENCE DESCRIPTION: SEQ ID NO: 23:

Asp Glu Leu Asn Pro Gln Lys Xaa Lys His Gln Gly Val Arg Lys
1               5                   10                  15

Ala Lys Xaa His Leu Gly Ile Arg
                20

(2) INFORMATION FOR SEQ ID NO: 24:

(i) SEQUENCE CHARACTERISTICS:
            (A) LENGTH: 19
            (B) TYPE: Amino acid
            (D) TOPOLOGY: Linear (xi) SEQUENCE DESCRIPTION: SEQ ID NO: 24:

Gln Leu Asp Tyr Glu Xaa Lys Val Val Asn Pro Tyr Tyr Leu Arg
1               5                   10                  15

VAL ARG ARG LYS (2) INFORMATION FOR SEQ ID NO: 25:

(i) SEQUENCE CHARACTERISTICS:
            (A) LENGTH: 25
            (B) TYPE: Amino acid
            (D) TOPOLOGY: Linear (xi) SEQUENCE DESCRIPTION: SEQ ID NO: 25:

Lys Met Ser Leu Gln Leu Tyr Gln Val Asp Ser Arg Thr Tyr Leu
1               5                   10                  15

Leu Asp Phe Arg Ser Ile Asp Asp Xaa Ile
                20                  25
```

(2) INFORMATION FOR SEQ ID NO: 26:

(i) SEQUENCE CHARACTERISTICS:
        (A) LENGTH: 18
        (B) TYPE: Amino acid
        (D) TOPOLOGY: Linear (xi) SEQUENCE DESCRIPTION: SEQ ID NO: 26:

```
Asp Ala Glu Ala Gln Gly Lys Ser Ser Glu Ala Ser Leu Thr Xaa
1               5                   10                  15
Ser Val Thr
```

(2) INFORMATION FOR SEQ ID NO: 27:

(i) SEQUENCE CHARACTERISTICS:
        (A) LENGTH: 17
        (B) TYPE: Amino acid
        (D) TOPOLOGY: Linear (xi) SEQUENCE DESCRIPTION: SEQ ID NO: 27:

```
Ile Gly His Tyr Ile Leu Gly Asp Thr Leu Gly Val Gly Thr Phe
1               5                   10                  15
Gly Lys
```

(2) INFORMATION FOR SEQ ID NO: 28:

(i) SEQUENCE CHARACTERISTICS:
        (A) LENGTH: 26
        (B) TYPE: Amino acid
        (D) TOPOLOGY: Linear (xi) SEQUENCE DESCRIPTION: SEQ ID NO: 28:

```
Leu Tyr Gln Val Ile Ser Thr Pro Ser Asp Ile Phe Met Val Met
1               5                   10                  15
Glu Tyr Val Ser Gly Gly Glu Leu Phe Asp Tyr
                20                  25
```

(2) INFORMATION FOR SEQ ID NO: 29:

(i) SEQUENCE CHARACTERISTICS:
        (A) LENGTH: 12
        (B) TYPE: Amino acid
        (D) TOPOLOGY: Linear (xi) SEQUENCE DESCRIPTION: SEQ ID NO: 29:

```
Arg Leu Phe Gln Gln Ile Leu Ser Gly Val Asp Tyr
1               5                   10
```

(2) INFORMATION FOR SEQ ID NO: 30:

(i) SEQUENCE CHARACTERISTICS:
        (A) LENGTH: 11
        (B) TYPE: Amino acid
        (D) TOPOLOGY: Linear (xi) SEQUENCE DESCRIPTION: SEQ ID NO: 30:

```
Asp Leu Lys Pro Glu Asn Val Leu Leu Asp Ala
1               5                   10
```

(2) INFORMATION FOR SEQ ID NO: 31:

(i) SEQUENCE CHARACTERISTICS:
        (A) LENGTH: 17
        (B) TYPE: Amino acid (D) TOPOLOGY: Linear (xi) SEQUENCE DESCRIPTION: SEQ ID NO: 31:

Ile Ala Asp Phe Gly Leu Ser Asn Met Met Ser Asp Gly Glu Phe
1               5                   10                  15

Leu Arg (2) INFORMATION FOR SEQ ID NO: 32:

(i) SEQUENCE CHARACTERISTICS:
        (A) LENGTH: 22
        (B) TYPE: Amino acid
        (D) TOPOLOGY: Linear (xi) SEQUENCE DESCRIPTION: SEQ ID NO: 32:

Lys Ile Xaa Asp Gly Ile Phe Tyr Thr Pro Gln Tyr Leu Asn Pro
1               5                   10                  15

Xaa Val Ile Xaa Leu Leu Lys
                20

(2) INFORMATION FOR SEQ ID NO: 33:

(i) SEQUENCE CHARACTERISTICS:
        (A) LENGTH: 5
        (B) TYPE: Amino acid
        (D) TOPOLOGY: Linear (xi) SEQUENCE DESCRIPTION: SEQ ID NO: 33:

Asp Ile Arg Glu His
1               5

(2) INFORMATION FOR SEQ ID NO: 34:

(i) SEQUENCE CHARACTERISTICS:
        (A) LENGTH: 20
        (B) TYPE: Amino acid
        (D) TOPOLOGY: Linear (xi) SEQUENCE DESCRIPTION: SEQ ID NO: 34:

Tyr Leu Phe Pro Glu Asp Pro Ser Tyr Ser Xaa Xaa Met Ile Asp
1               5                   10                  15

Asp Glu Ala Leu Lys
                20

(2) INFORMATION FOR SEQ ID NO: 35:

(i) SEQUENCE CHARACTERISTICS:
        (A) LENGTH: 16
        (B) TYPE: Amino acid
        (D) TOPOLOGY: Linear (xi) SEQUENCE DESCRIPTION: SEQ ID NO: 35:

Asn His Gln Asp Pro Leu Ala Val Ala Tyr His Leu Ile Ile Asp
1               5                   10                  15

Asn (2) INFORMATION FOR SEQ ID NO: 36:

(i) SEQUENCE CHARACTERISTICS:
        (A) LENGTH: 9
        (B) TYPE: Amino acid
        (D) TOPOLOGY: Linear (xi) SEQUENCE DESCRIPTION: SEQ ID NO: 36:

```
Asp Phe Tyr Leu Ala Thr Xaa Pro Pro
1               5
```

(2) INFORMATION FOR SEQ ID NO: 37:

(i) SEQUENCE CHARACTERISTICS:
        (A) LENGTH:  9
        (B) TYPE:  Amino acid
        (D) TOPOLOGY: Linear (xi) SEQUENCE DESCRIPTION:  SEQ ID NO: 37:

```
Asp Xaa Phe Leu Asp Asp His Xaa Leu
1               5
```

(2) INFORMATION FOR SEQ ID NO: 38:

(i) SEQUENCE CHARACTERISTICS:
        (A) LENGTH:  10
        (B) TYPE:  Amino acid
        (D) TOPOLOGY: Linear (xi) SEQUENCE DESCRIPTION:  SEQ ID NO: 38:

```
Val Pro Phe Leu Val Ala Glu Thr Pro Arg
1               5                   10
```

(2) INFORMATION FOR SEQ ID NO: 39:

(i) SEQUENCE CHARACTERISTICS:
        (A) LENGTH:  5
        (B) TYPE:  Amino acid
        (D) TOPOLOGY: Linear (xi) SEQUENCE DESCRIPTION:  SEQ ID NO: 39:

```
Trp His Leu Gly Ile
1               5
```

(2) INFORMATION FOR SEQ ID NO: 40:

(i) SEQUENCE CHARACTERISTICS:
        (A) LENGTH:  14
        (B) TYPE:  Amino acid
        (D) TOPOLOGY: Linear (xi) SEQUENCE DESCRIPTION:  SEQ ID NO: 40:

```
Xaa Gln Ser Arg Pro Asn Asp Ile Met Ala Glu Val Xaa Arg
1               5                   10
```

(2) INFORMATION FOR SEQ ID NO: 41:

(i) SEQUENCE CHARACTERISTICS:
        (A) LENGTH:  10
        (B) TYPE:  Amino acid
        (D) TOPOLOGY: Linear (xi) SEQUENCE DESCRIPTION:  SEQ ID NO: 41:

```
Val Val Asn Pro Tyr Tyr Leu Arg Val Arg
1               5                   10
```

(2) INFORMATION FOR SEQ ID NO: 42:

(i) SEQUENCE CHARACTERISTICS:
        (A) LENGTH:  18
        (B) TYPE:  Amino acid
        (D) TOPOLOGY: Linear (xi) SEQUENCE DESCRIPTION:  SEQ ID NO: 42:

```
Met Ser Leu Gln Leu Tyr Gln Val Asp Ser Arg Thr Tyr Leu Leu
```

(2) INFORMATION FOR SEQ ID NO: 43:

(i) SEQUENCE CHARACTERISTICS:
        (A) LENGTH: 12
        (B) TYPE: Amino acid
        (D) TOPOLOGY: Linear (xi) SEQUENCE DESCRIPTION: SEQ ID NO: 43:

```
Xaa Asp Ser Asp Ala Glu Ala Gln Gly Lys Pro Ser
1               5                   10
```

(2) INFORMATION FOR SEQ ID NO: 44:

(i) SEQUENCE CHARACTERISTICS:
        (A) LENGTH: 1647
        (B) TYPE: Nucleic acid
        (C) STRANDEDNESS: Single
        (D) TOPOLOGY: Linear (iv) ANTI-SENSE: No (xi) SEQUENCE DESCRIPTION: SEQ ID NO: 44:

```
ATGGCCGAGA AGCAGAAGCA CGACGGGCGG GTGAAGATCG GCCACTACAT          50
CCTGGGGGAC ACGCTGGGCG TCGGCACCTT CGGGAAAGTG AAGGTGGGCA         100
AGCACGAGTT GACTGGACAT AAAGTTGCTG TGAAGATACT CAACCGGCAG         150
AAGATTCGAA GCCTGGACGT GGTCGGGAAA ATCCGCAGAG AGATCCAGAA         200
CCTGAAGCTT TTCAGGCACC CTCATATAAT CAAACTGTAC CAGGTCATCA         250
GTACACCGTC TGATATTTTC ATGGTCATGG AATATGTCTC AGGAGGAGAG         300
CTATTTGATT ATATCTGTAA AAATGGAAGG TTGGACGAAA AGGAGAGTCG         350
ACGTCTGTTC CAGCAGATCC TTTCTGGTGT GGACTATTGT CACAGGCATA         400
TGGTGGTCCA CAGAGATTTG AAACCTGAAA ACGTCCTGCT TGATGCACAC         450
ATGAATGCAA AGATAGCCGA CTTCGGTCTT TCAAACATGA TGTCAGATGG         500
TGAATTTTTA AGAACGAGCT GTGGCTCGCC CAATTATGCT GCACCAGAAG         550
TAATTTCAGG AAGATTCTAC GCAGGCCCTG AAGTAGACAT CTGGAGCAGC         600
GGGGTCATTC TCTATGCTTT GCTGTGTGGA ACTCTCCCTT TTGATGATGA         650
CCACGTGCCA ACTCTTTTTA AGAAGATATG TGACGGGATA TTTTATACCC         700
CTCAGTATTT GAATCCCTCT GTAATAAGCC TTTTGAAGCA TATGCTGCAG         750
GTAGATCCTA TGAAGAGGGC CACAATAAAA GATATCAGGG AACATGAATG         800
GTTTAAGCAG GACCTTCCAA AATATCTCTT TCCTGAAGAC CCGTCTTATA         850
GTTCAACCAT GATTGATGAT GAAGCCTTAA AGAAGTGTGT GAGAAGTTC          900
GAGTGCTCAG AGGAGGAGGT CCTCAGCTGC CTGTACAACA GAAACCACCA         950
GGACCCACTG GCAGTTGCCT ACCACCTCAT AATAGACAAC AGGAGAATAA        1000
TGAACGAAGC CAAAGATTTC TACTTGGCAA CAAGCCCACC CGATTCTTTC        1050
CTCGATGATC ACCATTTAAC TCGGCCTCAC CCTGAGAGAG TACCATTCTT        1100
GGTTGCCGAA ACACCAAGGG CCCGACACAC CCTAGATGAA TTAAACCCAC        1150
AGAAATCCAA ACACCAAGGC GTACGGAAGG CAAAGTGGCA TTTGGGGATT        1200
CGAAGTCAAA GCCGACCCAA TGACATCATG GCAGAAGTGT GTAGAGCAAT        1250
```

| CAAGCAGTTG GACTATGAAT GGAAGGTTGT AAACCCCTAT TATTTGCGTG | 1300 |
| CAAGCAGTTG GACTATGAAT GGAAGGTTGT AAACCCCTAT TATTTGCGTG | 1300 |

```
CAAGCAGTTG GACTATGAAT GGAAGGTTGT AAACCCCTAT TATTTGCGTG          1300

TGCGAAGGAA GAACCCTGTG ACAAGCACAT TTTCCAAAAT GAGTCTACAG          1350

CTATACCAAG TGGATAGTAG GACTTACTTA TTGGATTTCC GAAGTATTGA          1400

TGATGAGATT ACAGAAGCCA AATCAGGGAC TGCTACTCCA CAGAGATCGG          1450

GATCCATCAG CAACTATCGA TCTTGCCAAA GGAGCGACTC CGACGCCGAG          1500

GCTCAAGGAA AGCCCTCAGA AGTCTCTCTT ACCTCATCCG TGACCTCCCT          1550

CGACTCCTCT CCTGTTGACG TAGCTCCAAG ACCAGGAAGT CACACGATAG          1600

AATTTTTTGA AATGTGTGCA AATCTAATTA AAATTCTTGC ACAGTAA             1647
```

(2) INFORMATION FOR SEQ ID NO: 45:

(i) SEQUENCE CHARACTERISTICS:
        (A) LENGTH: 20
        (B) TYPE: Amino Acid
        (D) TOPOLOGY: Linear (xi) SEQUENCE DESCRIPTION: SEQ ID NO: 45:

```
Asp Phe Tyr Leu Ala Thr Ser Pro Pro Asp Ser Phe Leu Asp Asp
1               5                   10                  15

His His Leu Thr Arg
            20
```

(2) INFORMATION FOR SEQ ID NO: 46:

(i) SEQUENCE CHARACTERISTICS:
        (A) LENGTH: 12
        (B) TYPE: Amino Acid
        (D) TOPOLOGY: Linear (xi) SEQUENCE DESCRIPTION: SEQ ID NO: 46:

```
Pro Leu Ser Arg Thr Leu Ser Val Ala Ala Lys Lys
1               5                   10
```

(2) INFORMATION FOR SEQ ID NO: 47:

(i) SEQUENCE CHARACTERISTICS:
        (A) LENGTH: 13
        (B) TYPE: Amino Acid
        (D) TOPOLOGY: Linear (xi) SEQUENCE DESCRIPTION: SEQ ID NO: 47:

```
Leu Lys Lys Leu Thr Leu Arg Ala Ser Phe Ser Ala Gln
1               5                   10
```

(2) INFORMATION FOR SEQ ID NO: 48:

(i) SEQUENCE CHARACTERISTICS:
        (A) LENGTH: 14
        (B) TYPE: Amino Acid
        (D) TOPOLOGY: Linear (xi) SEQUENCE DESCRIPTION: SEQ ID NO: 48:

```
Pro Gly Leu Lys Pro His Pro Glu Arg Met Pro Pro Leu Ile
1               5                   10
```

(2) INFORMATION FOR SEQ ID NO: 49:

(i) SEQUENCE CHARACTERISTICS:
        (A) LENGTH: 15
        (B) TYPE: Amino Acid
        (D) TOPOLOGY: Linear (xi) SEQUENCE DESCRIPTION: SEQ ID NO: 49:

His Met Arg Ser Ala Met Ser Gly Leu His Leu Val Lys Arg Arg
1               5                   10                  15

(2) INFORMATION FOR SEQ ID NO: 50:

(i) SEQUENCE CHARACTERISTICS:
        (A) LENGTH: 20
        (B) TYPE: Amino Acid
        (D) TOPOLOGY: Linear (xi) SEQUENCE DESCRIPTION: SEQ ID NO: 50:

Asp Phe Tyr Leu Ala Thr Ser Pro Pro Asp Ser Phe Leu Asp Asp
1               5                   10                  15

His His Leu Thr Arg
                20

(2) INFORMATION FOR SEQ ID NO: 51:

(i) SEQUENCE CHARACTERISTICS:
        (A) LENGTH: 15
        (B) TYPE: Amino Acid
        (D) TOPOLOGY: Linear (xi) SEQUENCE DESCRIPTION: SEQ ID NO: 51:

Met Asp Asp Ser Ala Met His Ile Pro Pro Gly Leu Lys Pro His
1               5                   10                  15

(2) INFORMATION FOR SEQ ID NO: 52:

(i) SEQUENCE CHARACTERISTICS:
        (A) LENGTH: 17
        (B) TYPE: Amino Acid
        (D) TOPOLOGY: Linear (xi) SEQUENCE DESCRIPTION: SEQ ID NO: 52:

Val Val Asp Ile Tyr Ser Lys Phe Asp Val Ile Asn Leu Ala Ala
1               5                   10                  15

Glu Lys (2) INFORMATION FOR SEQ ID NO: 53:

(i) SEQUENCE CHARACTERISTICS:
        (A) LENGTH: 19
        (B) TYPE: Amino Acid
        (D) TOPOLOGY: Linear (xi) SEQUENCE DESCRIPTION: SEQ ID NO: 53:

Gly Cys Gly Gly Ala Thr Cys Cys Gly Thr Asn Gly Ala Tyr Ala
1               5                   10                  15

Thr His Thr Ala (2) INFORMATION FOR SEQ ID NO: 54:

(i) SEQUENCE CHARACTERISTICS:
        (A) LENGTH: 22
        (B) TYPE: Amino Acid
        (D) TOPOLOGY: Linear (xi) SEQUENCE DESCRIPTION: SEQ ID NO: 54:

Cys Gly Gly Ala Ala Thr Thr Cys Tyr Thr Thr Tyr Thr Cys Asn
1               5                   10                  15

Gly Cys Asn Gly Cys Asn Ala

-continued

```
            20

(2) INFORMATION FOR SEQ ID NO: 55:

(i) SEQUENCE CHARACTERISTICS:
        (A) LENGTH:  8
        (B) TYPE:  Amino Acid
        (D) TOPOLOGY:  Linear (xi) SEQUENCE DESCRIPTION:  SEQ ID NO: 55:

Lys Phe Asp Val Ile Asn Leu Ala
1               5

(2) INFORMATION FOR SEQ ID NO: 56:

(i) SEQUENCE CHARACTERISTICS:
        (A) LENGTH:  23
        (B) TYPE:  Amino Acid
        (D) TOPOLOGY:  Linear (xi) SEQUENCE DESCRIPTION:  SEQ ID NO: 56:

Ala Ala Arg Thr Thr Tyr Gly Ala Tyr Gly Thr Asn Ala Thr His
1               5                   10                  15

Ala Ala Tyr Cys Thr Asn Gly Cys
            20

(2) INFORMATION FOR SEQ ID NO: 57:

(i) SEQUENCE CHARACTERISTICS:
        (A) LENGTH:  23
        (B) TYPE:  Amino Acid
        (D) TOPOLOGY:  Linear (xi) SEQUENCE DESCRIPTION:  SEQ ID NO: 57:

Ala Ala Arg Thr Thr Tyr Gly Ala Tyr Gly Thr Asn Ala Thr His
1               5                   10                  15

Ala Ala Tyr Thr Thr Arg Gly Cys
            20

(2) INFORMATION FOR SEQ ID NO: 58:

(i) SEQUENCE CHARACTERISTICS:
        (A) LENGTH:  23
        (B) TYPE:  Amino Acid
        (D) TOPOLOGY:  Linear (xi) SEQUENCE DESCRIPTION:  SEQ ID NO: 58:

Cys Thr Cys Cys Ala Ala Gly Thr Thr Gly Ala Thr Gly Thr
1               5                   10                  15

Thr Ala Thr Cys Ala Ala Cys Cys
            20

(2) INFORMATION FOR SEQ ID NO: 59:

(i) SEQUENCE CHARACTERISTICS:
        (A) LENGTH:  6
        (B) TYPE:  Amino Acid
        (D) TOPOLOGY:  Linear (xi) SEQUENCE DESCRIPTION:  SEQ ID NO: 59:

Glu Glu Leu Gln Ile Gly
1               5

(2) INFORMATION FOR SEQ ID NO: 60:
```

(i) SEQUENCE CHARACTERISTICS:
        (A) LENGTH: 7
        (B) TYPE: Amino Acid
        (D) TOPOLOGY: Linear (xi) SEQUENCE DESCRIPTION: SEQ ID NO: 60:

Phe Pro Lys Pro Glu Phe Met
1               5

(2) INFORMATION FOR SEQ ID NO: 61:

(i) SEQUENCE CHARACTERISTICS:
        (A) LENGTH: 1978
        (B) TYPE: Nucleic acid
        (C) STRANDEDNESS: Single
        (D) TOPOLOGY: Linear (iv) ANTI-SENSE: No (xi) SEQUENCE DESCRIPTION: SEQ ID NO: 61:

| | |
|---|---:|
| CTCGCTGCGG TCCAAGCAGG TAAAGCGGGG CTCGGCGAAC GCGCGCGACC | 50 |
| CGAGGGGCGT GGTCCGCGGT CCCGGGGGTC CCGGCCCGGC CCTTCCCGCT | 100 |
| TCCCTGTGTC CCCGCAGACA CTTCGCCATG GCAATACGA GCAGCGAGCG | 150 |
| CGCCGCGCTG GAGCGGCAGG CTGGCCATAA GACGCCGCGG AGGGACAGCT | 200 |
| CGGAGGGCAC CAAGGATGGG GACAGGCCCA AGATCCTGAT GGACAGCCCC | 250 |
| GAAGACGCCG ACATCTTCCA CACCGAGGAA ATGAAGGCTC CAGAGAAGGA | 300 |
| GGAGTTCCTG GCGTGGCAGC ACGACCTCGA GGTGAATGAG AAAGCCCCCG | 350 |
| CCCAGGCTCG GCCCACCGTA TTTCGATGGA CAGGGGTGG AAAGGAGGTC | 400 |
| TACTTGTCTG GATCCTTCAA CAACTGGAGC AAATTGCCCC TCACTAGAAG | 450 |
| CCAAAACAAC TTCGTAGCCA TCCTGGACCT NCCGGAAGGA GAGCATCAGT | 500 |
| ACAAGTTCTT TGTGGATGGC CAGTGGACCC ACGATCCTTC CGAGCCAATA | 550 |
| GTAACCAGCC AGCTTGGCAC AGTTAACAAC ATCATTCAAG TGAAGAAAAC | 600 |
| TGACTTTGAA GTATTTGATG CTTTAATGGT GGATTCCCAA AAGTGCTCCG | 650 |
| ATGTATCTGA GCTGTCCAGT TCCCCCCCAG GACCCTACCA CCAGGAGCCT | 700 |
| TACATCTCTA AACCAGAGGA GCGGTTCAAG GCCCCGCCCA TCCTCCCGCC | 750 |
| TCACCTGCTG CAGGTCATCT TGAACAAGGA CACGGGCATC TCTTGTGATC | 800 |
| CAGCGCTGCT TCCGGAGCCC AACCACGTCA TGCTGAACCA CCTCTATGCA | 850 |
| CTCTCTATCA AGGATGGAGT GATGGTGCTC AGTGCGACCC ATCGGTACAA | 900 |
| GAAAAAGTAC GTCACCACCC TCCTCTACAA GCCCATATGA GAGGATGAGC | 950 |
| CAGCCGTGGG CCACGGGACA GCAGGCGGGA GCCGCTGGGC TCTCCGTGTG | 1000 |
| CATGCGCATC CTCACTCCGG GACATCTCAC CCCCACATAG TCCTCCTTGA | 1050 |
| AGGTCTGTCC AGGCACAGCC AGAAATCGGA TGGACGGCAG ACCGTGGTCC | 1100 |
| CAGCACCGCA GGCAGTGCGC CAGGCTCTAG TGCTCTAAGC ATCATCCCTC | 1150 |
| TGCTGGCCCG AGATGTCTAC AGCCAGACCT GAATGCTGGT TCCTGCTAGA | 1200 |
| AAACCTAGGA CAGGAACTGA AGTCACCAAA GCCCTCATCA TCCCTGCTGA | 1250 |
| AGCCTGGCTT GGAAGAAAGC AGTGCTCGGT CTTGCCTGTC CTTCCGAATC | 1300 |
| ACAGCAGTAG ATTGTAGACT CCATGGAATT TCAGTGTCCA ATTTCCAGAT | 1350 |
| GCAGCTTCGC AATCGATTCC TGACACTGTG CACTGAGACC TTCTTAACCA | 1400 |

```
GAGTGGCTGG CTGTCCACTC TCACTTAAGG CAATAAGTCA CCAGGACGAG         1450

ACTATAGGTC ATGTGACTAC TGAGCAATAA TCGTTCTCAN ACAGACATCA         1500

GAAACCACTG CCATTTCTCC ATCAAGCCAG ACGATCCTGA GGACTGACCA         1550

CCATGGGAGG TTGTCCACCT TATTTCAGTT GCAGTGTTGG CCATGTTACC         1600

GTGACAACCT GGTCGAAGTG CCCGCCCTCT TTTTAGTTCT AGCACGTGCT         1650

ACTCAGCTGG GGGCCGTGTC TCCAGTGAGC AGAGAGTGTA CACGGTGGTT         1700

ACTATTGCCT GATCCTAAGA GAGCTTGGCA CCCTGCGGCA GACTGCTAGG         1750

TTCCAGCAGG GTTGGCACGA GTGAACCTAT GTGTGCTCAG TGTGATTTCC         1800

ACAGTGATGT CACAGACGTG CCCATTGGTA CAGGCTCCTG TCACCTGTCA         1850

GCATAGGTAG GCACAAGCTC TGTGGTGTCC GCTATTTGGT TAAACCTGAG         1900

TTTTGGGTAC CTTTTGTTAC TGTTTTCAAA ACACGGACTT GCTGTCATCT         1950

TGATGTACAA GTTTCAATAA AGCTTTGG                                 1978
```

(2) INFORMATION FOR SEQ ID NO: 62:

(i) SEQUENCE CHARACTERISTICS:
        (A) LENGTH: 270
        (B) TYPE: Amino Acid
        (D) TOPOLOGY: Linear (xi) SEQUENCE DESCRIPTION: SEQ ID NO: 62:

```
Met Gly Asn Thr Ser Ser Glu Arg Ala Ala Leu Glu Arg Gln Ala
1               5                   10                  15

Gly His Lys Thr Pro Arg Arg Asp Ser Ser Glu Gly Thr Lys Asp
                20                  25                  30

Gly Asp Arg Pro Lys Ile Leu Met Asp Ser Pro Glu Asp Ala Asp
                35                  40                  45

Ile Phe His Thr Glu Glu Met Lys Ala Pro Glu Lys Glu Glu Phe
                50                  55                  60

Leu Ala Trp Gln His Asp Leu Glu Val Asn Glu Lys Ala Pro Ala
                65                  70                  75

Gln Ala Arg Pro Thr Val Phe Arg Trp Thr Gly Gly Gly Lys Glu
                80                  85                  90

Val Tyr Leu Ser Gly Ser Phe Asn Asn Trp Ser Lys Leu Pro Leu
                95                  100                 105

Thr Arg Ser Gln Asn Asn Phe Val Ala Ile Leu Asp Leu Pro Glu
                110                 115                 120

Gly Glu His Gln Tyr Lys Phe Phe Val Asp Gly Gln Trp Thr His
                125                 130                 135

Asp Pro Ser Glu Pro Ile Val Thr Ser Gln Leu Gly Thr Val Asn
                140                 145                 150

Asn Ile Ile Gln Val Lys Lys Thr Asp Phe Glu Val Phe Asp Ala
                155                 160                 165

Leu Met Val Asp Ser Gln Lys Cys Ser Asp Val Ser Glu Leu Ser
                170                 175                 180

Ser Ser Pro Pro Gly Pro Tyr His Gln Glu Pro Tyr Ile Ser Lys
                185                 190                 195

Pro Glu Glu Arg Phe Lys Ala Pro Pro Ile Leu Pro Pro His Leu
                200                 205                 210

Leu Gln Val Ile Leu Asn Lys Asp Thr Gly Ile Ser Cys Asp Pro
                215                 220                 225
```

```
Ala Leu Leu Pro Glu Pro Asn His Val Met Leu Asn His Leu Tyr
            230                 235                 240

Ala Leu Ser Ile Lys Asp Gly Val Met Val Leu Ser Ala Thr His
            245                 250                 255

Arg Tyr Lys Lys Lys Tyr Val Thr Thr Leu Leu Tyr Lys Pro Ile
            260                 265                 270
```

(2) INFORMATION FOR SEQ ID NO: 63:

(i) SEQUENCE CHARACTERISTICS:
        (A) LENGTH: 1576
        (B) TYPE: Nucleic acid
        (C) STRANDEDNESS: Single
        (D) TOPOLOGY: Linear (iv) ANTI-SENSE: No (xi) SEQUENCE DESCRIPTION: SEQ ID NO: 63:

```
GCGCCCTTAA AGATGGTGAG GGGGCTATGC TCTGAGTAGA AGGTGGTGAC            50

CTCCAGGAGC GGTGGGATGA TGAGGGCCCG GGCGCCTCTT GCAATGGAGA           100

CGGTCATTTC TTCAGATAGC TCCCCAGCTG TGGAAAATGA GCATCCTCAA           150

GAGACCCCAG AATCCAACAA TAGCGTGTAT ACTTCCTTCA TGAAGTCTCA           200

TCGCTGCTAT GACCTGATTC CCACAAGCTC CAAATTGGTT GTATTTGATA           250

CGTCCCTGCA GGTGAAGAAA GCTTTTTTTG CTTTGGTGAC TAACGGTGTA           300

CGAGCTGCCC CTTTATGGGA TAGTAAGAAG CAAAGTTTTG TGGGCATGCT           350

GACCATCACT GATTTCATCA ATATCCTGCA CCGCTACTAT AAATCAGCGT           400

TGGTACAGAT CTATGAGCTA GAAGAACACA AGATAGAAAC TTGGAGAGAG           450

GTGTATCTCC AGGACTCCTT TAAACCGCTT GTCTGCATTT CTCCTAATGC           500

CAGCTTGTTT GATGCTGTCT CTTCATTAAT TCGCAACAAG ATCCACAGGC           550

TGCCAGTTAT TGACCCAGAA TCAGGCAATA CTTTGTACAT CCTCACCCAC           600

AAGCGCATTC TGAAGTTCCT CAAATTGTTT ATCACTGAGT TCCCCAAGCC           650

AGAGTTCATG TCCAAGTCTC TGGAAGAGCT ACAGATTGGC ACCTATGCCA           700

ATATTGCTAT GGTTCGCACT ACCACCCCCG TCTATGTGGC TCTGGGGATT           750

TTTGTACAGC ATCGAGTCTC AGCCCTGCCA GTGGTGGATG AGAAGGGGCG           800

TGTGGTGGAC ATCTACTCCA AGTTTGATGT TATCAATCTG GCAGCAGAAA           850

AGACCTACAA CAACCTAGAT GTATATGTGA CTAAAGCCTT GCAACATCGA           900

TCACATTACT TTGAGGGTGT CTCAAGTGC TACCTGCATG AGACTCTGGA           950

GACCATCATC AACAGGCTAG TGGAAGCAGA GGTTCACCGA CTTGTAGTGG          1000

TGGATGAAAA TGATGTGGTC AAGGGAATTG TATCACTGTC TGACATCCTG          1050

CAGGCCCTGG TGCTCACAGG TGGAGAGAAG AAGCCCTGAG CTGGGGAAGG          1100

GGTCATGCAG CACCAGGGGA TATGCCCAAC TCACTGCCTG CTGGAAGCTC          1150

TGTGGGAATC AGATGAAACT TGAGGGAATT GTGACTCTGT TCCCTGTTCA          1200

GGGTCCCCTG CCCTTCTATC TGGGAGCTAG GGAAGGTATG GGGGAGGAAA          1250

GAGAATGGAT TTATAGCTAC CCTTACCCTC ACACATACAC TTGAAAAAAC          1300

TTTCAGCCTA GCCAGTTCTA GCCCCTGTCC TCTTAGATAT ATCCCCCTTT          1350

CTGGGTGAAC TATAGGCTCT GTGCCTCTCA GACAAATTCT GATCTCTAAG          1400

AGATCCCCAG ACCTCACTTG CCTCTGCCTC CATCTTGGCC CTGATTCAAC          1450
```

```
CCTAAGATAA TAGCACAACA AAATTCTTCA TAAAGATATT TTTATTCACC           1500

TGTTCCGTGC TATATGGAGG AGGCCAAGTC CATTTAGTGA CATTTCTTCC           1550

CATAATGTGA GTGGGAGGA TTGTGG                                      1576
```

(2) INFORMATION FOR SEQ ID NO: 64:

(i) SEQUENCE CHARACTERISTICS:
        (A) LENGTH: 331
        (B) TYPE: Amino Acid
        (D) TOPOLOGY: Linear (xi) SEQUENCE DESCRIPTION: SEQ ID NO: 64:

```
Met Glu Thr Val Ile Ser Ser Asp Ser Ser Pro Ala Val Glu Asn
1               5                   10                  15

Glu His Pro Gln Glu Thr Pro Glu Ser Asn Asn Ser Val Tyr Thr
                20                  25                  30

Ser Phe Met Lys Ser His Arg Cys Tyr Asp Leu Ile Pro Thr Ser
                35                  40                  45

Ser Lys Leu Val Val Phe Asp Thr Ser Leu Gln Val Lys Lys Ala
                50                  55                  60

Phe Phe Ala Leu Val Thr Asn Gly Val Arg Ala Ala Pro Leu Trp
                65                  70                  75

Asp Ser Lys Lys Gln Ser Phe Val Gly Met Leu Thr Ile Thr Asp
                80                  85                  90

Phe Ile Asn Ile Leu His Arg Tyr Tyr Lys Ser Ala Leu Val Gln
                95                  100                 105

Ile Tyr Glu Leu Glu Glu His Lys Ile Glu Thr Trp Arg Glu Val
                110                 115                 120

Tyr Leu Gln Asp Ser Phe Lys Pro Leu Val Cys Ile Ser Pro Asn
                125                 130                 135

Ala Ser Leu Phe Asp Ala Val Ser Ser Leu Ile Arg Asn Lys Ile
                140                 145                 150

His Arg Leu Pro Val Ile Asp Pro Glu Ser Gly Asn Thr Leu Tyr
                155                 160                 165

Ile Leu Thr His Lys Arg Ile Leu Lys Phe Leu Lys Leu Phe Ile
                170                 175                 180

Thr Glu Phe Pro Lys Pro Glu Phe Met Ser Lys Ser Leu Glu Glu
                185                 190                 195

Leu Gln Ile Gly Thr Tyr Ala Asn Ile Ala Met Val Arg Thr Thr
                200                 205                 210

Thr Pro Val Tyr Val Ala Leu Gly Ile Phe Val Gln His Arg Val
                215                 220                 225

Ser Ala Leu Pro Val Val Asp Glu Lys Gly Arg Val Val Asp Ile
                230                 235                 240

Tyr Ser Lys Phe Asp Val Ile Asn Leu Ala Ala Glu Lys Thr Tyr
                245                 250                 255

Asn Asn Leu Asp Val Ser Val Thr Lys Ala Leu Gln His Arg Ser
                260                 265                 270

His Tyr Phe Glu Gly Val Leu Lys Cys Tyr Leu His Glu Thr Leu
                275                 280                 285

Glu Thr Ile Ile Asn Arg Leu Val Glu Ala Glu Val His Arg Leu
                290                 295                 300

Val Val Val Asp Glu Asn Asp Val Val Lys Gly Ile Val Ser Leu
                305                 310                 315
```

```
Ser Asp Ile Leu Gln Ala Leu Val Leu Thr Gly Gly Glu Lys Lys
            320                 325                 330
Pro
```